(12) United States Patent
Cashman et al.

(10) Patent No.: US 8,996,392 B2
(45) Date of Patent: Mar. 31, 2015

(54) MEDICAL KIOSK AND METHOD OF USE

(75) Inventors: Steve Cashman, Powell, OH (US); John W. Spirk, Gates Mills, OH (US); Jason G. Tilk, Cleveland Hts., OH (US); John R. Nottingham, Bratenahl, OH (US); Jeffrey Kalman, Cleveland Hts, OH (US)

(73) Assignee: Healthspot, Inc., Dublin, OH (US)

( * ) Notice: Subject to any disclaimer, the term of this patent is extended or adjusted under 35 U.S.C. 154(b) by 244 days.

(21) Appl. No.: 13/314,473

(22) Filed: Dec. 8, 2011

(65) Prior Publication Data

US 2012/0253837 A1 Oct. 4, 2012

Related U.S. Application Data

(63) Continuation-in-part of application No. 29/403,857, filed on Oct. 12, 2011, now Pat. No. Des. 694,909.

(60) Provisional application No. 61/469,851, filed on Mar. 31, 2011, provisional application No. 61/541,719, filed on Sep. 30, 2011.

(51) Int. Cl.
| | |
|---|---|
| *G06Q 50/00* | (2012.01) |
| *G06Q 50/22* | (2012.01) |
| *E04H 1/12* | (2006.01) |
| *E04H 3/08* | (2006.01) |
| *G06F 19/00* | (2011.01) |
| *G06Q 10/10* | (2012.01) |
| *H04N 7/14* | (2006.01) |

(52) U.S. Cl.
CPC .............. *G06Q 50/22* (2013.01); *E04H 1/1205* (2013.01); *E04H 3/08* (2013.01); *G06F 19/3418* (2013.01); *G06Q 10/10* (2013.01); *H04N 7/141* (2013.01)

USPC ............................................................. 705/2

(58) Field of Classification Search
USPC ............... 4/612; 52/36.2, 79, 79.1, 79.5, 241; 62/259.1; 348/14.04; 378/62; 454/187; 600/300, 301; 705/2; 422/24; 200/61.61

See application file for complete search history.

(56) References Cited

U.S. PATENT DOCUMENTS

| | | | |
|---|---|---|---|
| 3,838,545 A | * | 10/1974 | Kump ............................ 52/79.8 |
| 4,884,514 A | | 12/1989 | Shockey et al. |
| 5,036,779 A | | 8/1991 | Capraro |
| D334,985 S | | 4/1993 | D'Agostino et al. |
| D344,140 S | | 2/1994 | Webster |
| 5,393,964 A | | 2/1995 | Hamilton et al. |
| 5,441,047 A | | 8/1995 | David et al. |
| 5,544,649 A | | 8/1996 | David et al. |
| 5,558,638 A | | 9/1996 | Evers et al. |
| 5,619,991 A | | 4/1997 | Sloane |

(Continued)

OTHER PUBLICATIONS

U.S. Searching Authority, International Search Report and Written Opinion, dated Apr. 19, 2013, for related application PCT/US13/24911.

*Primary Examiner* — John Pauls
(74) *Attorney, Agent, or Firm* — Fay Sharpe LLP

(57) ABSTRACT

A medical kiosk having a modular configuration and designed to provide tele-med services to a user. The medical kiosk includes first and second front panels, first and second rear panels, an interior chamber, a chamber access opening, and a user video conferencing system in the interior chamber. The user video conferencing system is designed to enable the user in the interior chamber to have a real-time or near real-time tele-conference with a medical provider located remotely from the medical kiosk.

18 Claims, 12 Drawing Sheets

(56) References Cited

U.S. PATENT DOCUMENTS

| | | |
|---|---|---|
| 5,646,605 A * | 7/1997 | Leonaggeo et al. ......... 340/5.64 |
| 5,660,176 A | 8/1997 | Iliff |
| 5,727,353 A | 3/1998 | Getz et al. |
| 5,801,755 A | 9/1998 | Echerer |
| 5,810,747 A | 9/1998 | Brudny et al. |
| 5,868,669 A | 2/1999 | Iliff |
| 5,897,493 A | 4/1999 | Brown |
| 5,910,107 A | 6/1999 | Iliff |
| 5,987,519 A | 11/1999 | Peifer et al. |
| 5,997,476 A | 12/1999 | Brown |
| 6,007,459 A | 12/1999 | Burgess |
| 6,022,315 A | 2/2000 | Iliff |
| 6,046,761 A | 4/2000 | Echerer |
| 6,071,236 A | 6/2000 | Iliff |
| 6,101,478 A | 8/2000 | Brown |
| 6,113,540 A | 9/2000 | Iliff |
| 6,205,716 B1 | 3/2001 | Peltz |
| 6,206,829 B1 | 3/2001 | Iliff |
| 6,224,548 B1 | 5/2001 | Gopinathan et al. |
| 6,248,064 B1 | 6/2001 | Gopinathan et al. |
| 6,248,065 B1 | 6/2001 | Brown |
| 6,270,455 B1 | 8/2001 | Brown |
| 6,295,767 B1 | 10/2001 | Barnhill et al. |
| 6,302,844 B1 | 10/2001 | Walker et al. |
| 6,368,273 B1 | 4/2002 | Brown |
| 6,369,847 B1 | 4/2002 | James et al. |
| 6,381,577 B1 | 4/2002 | Brown |
| 6,403,897 B1 | 6/2002 | Bluth et al. |
| 6,428,124 B1 | 8/2002 | Bluth et al. |
| 6,449,001 B1 | 9/2002 | Levy et al. |
| 6,511,435 B1 | 1/2003 | Bluth et al. |
| 6,540,673 B2 | 4/2003 | Gopinathan et al. |
| 6,594,607 B2 | 7/2003 | Lavery |
| 6,595,918 B2 | 7/2003 | Gopinathan et al. |
| 6,638,218 B2 | 10/2003 | Bulat |
| 6,641,532 B2 | 11/2003 | Iliff |
| 6,668,375 B1 | 12/2003 | Leovac |
| 6,692,436 B1 | 2/2004 | Bluth et al. |
| 6,725,209 B1 | 4/2004 | Iliff |
| 6,731,324 B2 | 5/2004 | Levy |
| 6,748,353 B1 | 6/2004 | Iliff |
| 6,790,178 B1 | 9/2004 | Mault et al. |
| 6,850,889 B1 | 2/2005 | Zayas, Jr. |
| 6,968,375 B1 | 11/2005 | Brown |
| 7,011,629 B2 | 3/2006 | Bulat |
| D521,155 S | 5/2006 | Shipard |
| D526,065 S | 8/2006 | Shipard |
| 7,112,175 B2 | 9/2006 | Gopinathan et al. |
| 7,188,151 B2 | 3/2007 | Kumar et al. |
| 7,223,236 B2 | 5/2007 | Brown |
| 7,252,636 B2 | 8/2007 | Brown |
| 7,297,109 B2 | 11/2007 | Brown |
| 7,297,111 B2 | 11/2007 | Iliff |
| 7,300,402 B2 | 11/2007 | Iliff |
| 7,310,668 B2 | 12/2007 | Brown |
| 7,320,030 B2 | 1/2008 | Brown |
| D577,127 S | 9/2008 | Ronco |
| 7,435,222 B2 | 10/2008 | Gopinathan et al. |
| 7,516,192 B2 | 4/2009 | Brown |
| 7,533,171 B2 | 5/2009 | Brown |
| 7,587,469 B2 | 9/2009 | Brown |
| 7,613,620 B2 | 11/2009 | Salwan |
| 7,624,028 B1 | 11/2009 | Brown |
| 7,691,059 B2 | 4/2010 | Bulat |
| 7,707,270 B2 | 4/2010 | Brown |
| 7,730,177 B2 | 6/2010 | Brown |
| 7,734,718 B2 | 6/2010 | Brown |
| 7,753,845 B2 | 7/2010 | Gopinathan et al. |
| 7,761,312 B2 | 7/2010 | Brown |
| 7,818,183 B2 | 10/2010 | Schoenberg |
| 7,822,625 B2 | 10/2010 | Brown |
| 7,831,444 B2 | 11/2010 | Brown |
| 7,860,725 B2 | 12/2010 | Gopinathan et al. |
| 7,870,249 B2 | 1/2011 | Brown |
| 7,877,271 B2 | 1/2011 | Brown |
| 7,904,310 B2 | 3/2011 | Brown |
| 7,912,733 B2 | 3/2011 | Clements et al. |
| RE42,288 E | 4/2011 | Degioanni |
| 7,921,186 B2 | 4/2011 | Brown |
| D638,551 S | 5/2011 | Gann |
| 7,941,323 B2 | 5/2011 | Brown |
| 7,941,326 B2 | 5/2011 | Brown |
| 7,941,327 B2 | 5/2011 | Brown |
| 7,949,383 B2 | 5/2011 | Cable et al. |
| 7,970,620 B2 | 6/2011 | Brown |
| 7,970,633 B2 | 6/2011 | Bulat |
| 7,979,284 B2 | 7/2011 | Brown |
| 7,987,100 B2 | 7/2011 | Brown |
| 8,005,691 B2 | 8/2011 | Kumar et al. |
| 8,015,025 B2 | 9/2011 | Brown |
| 8,015,138 B2 | 9/2011 | Illiff |
| 8,027,809 B2 | 9/2011 | Brown |
| 8,078,407 B1 | 12/2011 | Brown |
| 8,078,431 B2 | 12/2011 | Brown |
| 8,095,340 B2 | 1/2012 | Brown |
| 8,096,083 B2 | 1/2012 | Ma et al. |
| 8,140,663 B2 | 3/2012 | Brown |
| D664,667 S | 7/2012 | Krymov et al. |
| 8,260,630 B2 | 9/2012 | Brown |
| 8,285,560 B2 | 10/2012 | Gopinathan et al. |
| 8,321,284 B2 | 11/2012 | Clements et al. |
| 8,337,409 B2 | 12/2012 | Iliff |
| 2001/0011224 A1 | 8/2001 | Brown |
| 2003/0028399 A1 | 2/2003 | Davis et al. |
| 2003/0088441 A1 | 5/2003 | McNerney |
| 2003/0163351 A1 | 8/2003 | Brown et al. |
| 2004/0006496 A1 | 1/2004 | Nickerson |
| 2004/0019259 A1 | 1/2004 | Brown |
| 2004/0019261 A1 | 1/2004 | Gopinathan et al. |
| 2004/0019503 A1 | 1/2004 | Berenguer |
| 2004/0107116 A1 | 6/2004 | Brown |
| 2004/0230458 A1 | 11/2004 | Takayama et al. |
| 2004/0249778 A1 | 12/2004 | Iliff |
| 2005/0071916 A1 * | 4/2005 | Rooke et al. ...................... 4/612 |
| 2005/0228883 A1 | 10/2005 | Brown |
| 2005/0256739 A1 | 11/2005 | Brown |
| 2006/0010014 A1 | 1/2006 | Brown |
| 2006/0069753 A1 | 3/2006 | Hu et al. |
| 2006/0080152 A1 | 4/2006 | Brown |
| 2006/0189853 A1 | 8/2006 | Brown |
| 2006/0200319 A1 | 9/2006 | Brown |
| 2006/0217056 A1 * | 9/2006 | Gomi et al. ................... 454/187 |
| 2006/0235722 A1 | 10/2006 | Brown |
| 2006/0241975 A1 | 10/2006 | Brown |
| 2006/0259201 A1 | 11/2006 | Brown |
| 2006/0259332 A1 | 11/2006 | Brown |
| 2006/0271214 A1 | 11/2006 | Brown |
| 2006/0285660 A1 | 12/2006 | Brown |
| 2006/0285736 A1 | 12/2006 | Brown |
| 2006/0287889 A1 | 12/2006 | Brown |
| 2006/0287931 A1 | 12/2006 | Brown |
| 2006/0293572 A1 | 12/2006 | Bulat |
| 2007/0011320 A1 | 1/2007 | Brown |
| 2007/0016445 A1 | 1/2007 | Brown |
| 2007/0021984 A1 | 1/2007 | Brown |
| 2007/0061167 A1 | 3/2007 | Brown |
| 2007/0073113 A1 | 3/2007 | Squilla et al. |
| 2007/0118588 A1 | 5/2007 | Brown |
| 2007/0130287 A1 | 6/2007 | Kumar et al. |
| 2007/0156893 A1 | 7/2007 | Brown |
| 2007/0168242 A1 | 7/2007 | Brown |
| 2007/0168504 A1 | 7/2007 | Brown |
| 2007/0213605 A1 | 9/2007 | Brown |
| 2007/0265869 A1 | 11/2007 | Ryckman et al. |
| 2007/0299321 A1 | 12/2007 | Brown |
| 2008/0051638 A1 | 2/2008 | Iliff |
| 2008/0051640 A1 | 2/2008 | Iliff |
| 2008/0052119 A1 | 2/2008 | Iliff |
| 2008/0052318 A1 | 2/2008 | Iliff |
| 2008/0059247 A1 | 3/2008 | Iliff |
| 2008/0162393 A1 | 7/2008 | Iliff |
| 2008/0213128 A1 * | 9/2008 | Rudy et al. ...................... 422/24 |
| 2009/0083066 A1 | 3/2009 | Bailey et al. |
| 2009/0143652 A1 * | 6/2009 | Warburton et al. ............ 600/301 |

(56) References Cited

U.S. PATENT DOCUMENTS

| | | |
|---|---|---|
| 2009/0240115 A1 | 9/2009 | Bluth |
| 2009/0240116 A1 | 9/2009 | Bluth |
| 2009/0240524 A1 | 9/2009 | Bluth |
| 2009/0240527 A1 | 9/2009 | Bluth |
| 2009/0240528 A1 | 9/2009 | Bluth |
| 2009/0240702 A1 | 9/2009 | Bluth |
| 2009/0241177 A1 | 9/2009 | Bluth |
| 2010/0030580 A1 | 2/2010 | Salwan |
| 2010/0146300 A1 | 6/2010 | Brown |
| 2010/0274835 A1 | 10/2010 | Brown |
| 2011/0004487 A1 | 1/2011 | Schoenberg |
| 2011/0009707 A1 | 1/2011 | Kaundinya et al. |
| 2011/0106557 A1 | 5/2011 | Gazula |
| 2011/0122995 A1* | 5/2011 | Ferro, Jr. .................. 378/62 |
| 2011/0161475 A1 | 6/2011 | Raghavendran et al. |
| 2011/0191117 A1 | 8/2011 | Hashim-Waris |
| 2011/0288888 A1 | 11/2011 | Gazula |
| 2012/0004525 A1 | 1/2012 | Brown |
| 2012/0130647 A1 | 5/2012 | Brown |
| 2012/0130739 A1 | 5/2012 | Crane |
| 2012/0179479 A1* | 7/2012 | Waterson et al. .................. 705/2 |
| 2012/0185278 A1 | 7/2012 | Brown |
| 2012/0203466 A1 | 8/2012 | Brown |
| 2012/0253837 A1 | 10/2012 | Cashman |
| 2013/0013333 A1 | 1/2013 | Gopinathan et al. |

* cited by examiner

MEDICAL KIOSK AND METHOD OF USE

The present invention claims priority on U.S. Patent Application Ser. Nos. 61/469,851 file Mar. 31, 2011 and 61/541,719 filed Sep. 30, 2011, which are both incorporated herein by reference. The present invention also is a continuation-in-part of U.S. Design patent application Ser. No. 29/403,857 filed Oct. 12, 2011 now U.S. Pat. No. D694909, which is incorporated herein by reference.

The present invention is directed to medical services, more particularly to a method and device for providing medical services to individuals, even more particularly to a method and device for providing medical services to individuals at locations that traditionally have not provided medical services, and still even more particularly to a medical kiosk and method for using a medical kiosk to providing medical services to individuals at locations that are remote from a medical provider.

BACKGROUND OF THE INVENTION

Medical services are traditionally provided to individuals at a doctor's office or medical facility. Typically, an individual contacts his/her medical provider when the individual requires some type of medical assistance. The medical provider then sets an appointment time and date for the individual to see the medical provider. Many times, the time and date of the appointment are inconvenient for the individual. Furthermore, the individual seeking medical assistance may desire or need more immediate medical assistance and cannot wait for the time and date set by the medical provider. In such situations, the individual goes to the emergency room of a hospital or some type of medical clinic (e.g., Minute Clinic, Take Care Clinic, Urgent Care Clinic, etc.), assuming that such clinics are available or convenient to visit.

The costs associated with visiting a medical provider can be costly depending on the type of insurance, if any, the individual carries. When an individual visits the emergency room of a hospital, the medical costs can be substantially higher and insurance coverage may be limited to various types of visits. Insurance coverage and cost of the visit may also vary at various clinics. In many communities, clinics are not readily available, thus the individual must either visit the medical provider or go to the hospital.

Various pharmacy and drug stores have begun offering medical services on their premises. These locations generally offer flu shots and very basic medical services, and are typically provided by a nurse practitioner, not a doctor. As such, only very limited types of medical services are offered at such locations. Also, these locations are not offered in a private environment. Generally, the services are provided in a side corridor or partitioned location in the facility.

In view of the current state of the medical services, there is a need for providing medical services in a more convenient, desirable, timely and cost effective manner.

SUMMARY OF THE INVENTION

The present invention is directed to a method and device for providing medical services, diagnoses, health, and/or wellness advice to individuals in a convenient, desirable, timely and cost effective manner. The novel medical device of the present invention and the novel method for providing medical services, diagnoses, health advice, and/or wellness advice addresses the current deficiencies that exist for providing medical services to individuals.

In one non-limiting aspect of the invention, there is provided a remote medical service arrangement wherein a patient can receive various types of medical advice and services remotely from a medical provider (e.g., doctor, nurse practitioner, nurse, psychologist, optometrist, physician assistance, pharmacist, health coach, etc.). Traditionally, a patient was required to go to a medical facility (e.g., hospital, medical clinic, doctor's office, etc.) to personally meet with and be diagnosed by the medical provider. The present invention is directed to a method wherein medical services, diagnoses, health advice, and/or wellness advice can be dispensed by a medical provider at a location that is remote from the patient. In one non-limiting arrangement, there is provided an audio and/or video link between one or more medical providers located at one or more locations (e.g., medical provider's office, medical provider's home, hospital, etc.) and the patient is located at some other location (e.g., shopping mall, shopping center, drug store, grocery store, department store, warehouse store, discount retailer, discount department store, truck trailer, mobile office, mobile home, office space location, etc.) that is remote from the one or more medical providers. The novel method for providing medical services, diagnoses, health advice, and/or wellness advice enables a medical provider to provide medical services, diagnoses, health advice, and/or wellness advice to patients without the patient having to physically visit the medical provider and/or having to go to the medical provider's office or place of work. As can be appreciated, the audio and/or video link that is used by the medical provider can enable the medical provider to provide medical services, diagnoses, health advice, and/or wellness advice at a single remote location or a plurality of remote locations. When the audio and/or video link enables the medical provider to provide medical services, diagnoses, health advice, and/or wellness advice to a plurality of remote locations, a single medical provider and/or a plurality of medical providers can be used to provide medical services, diagnoses, health advice, and/or wellness advice to patients that are located at a variety of different remote locations. When a plurality of medical providers is used, the medical providers can be located at the same or different locations. As can be appreciated, the novel method for providing medical services allows for more flexibility for a patient to obtain medical services, diagnoses, health advice, and/or wellness advice. The site at which the patient obtains the medical services, diagnoses, health advice, and/or wellness advice can be located in non-traditional locations that are more convenient to a patient and/or can be located at multiple locations to provide easier and/or more convenient access to such medical services, diagnoses, health advice, and/or wellness advice. The multiple locations can be located in a single neighborhood, multiple neighborhoods, a single town or city, multiple towns or cities, a single state or province, multiple states or provinces, a single country, or multiple countries. The novel method can also be used to provide medical services, diagnoses, health advice, and/or wellness advice at non-standard hours (e.g., evening hours, weekend hours, holiday hours, etc.) to enable a patient to obtain medical services, diagnoses, health advice, and/or wellness advice that are more convenient and timely to the patient.

In another and/or alternative non-limiting aspect of the invention, the novel method of the present invention can be used to provide a variety of different medical services, diagnoses, health advice, and/or wellness advice. Non-limiting examples of such medical services, diagnoses, health advise, wellness advise and/or medical conditions that can be identified, treated and/or addressed include, but are not limited to Acid Reflux, Hypertension Management, Allergies, Athlete's Foot, Acne, Mental Health Counseling, Wellness Counseling, Asthma, Cold Sores, Vaccinations, Arthritis, Bronchitis, Impetigo, Wellness Coaching, Weight Loss, Eating Disorders, Bladder Infections, Insect Stings, Allergic Reactions, Hemorrhoids, Minor Burns, Health Risk Management, Migraine Headaches, Common Colds, Minor Skin Infections, Chronic Disease Management, Coughs, Poison Oak/Ivy, Diarrhea, Rashes, Diabetes, Ringworm, Lice, Ear Infections, Sties, Flu, Fever, Gout, Headache (minor), Pink Eye, Sinus Infections, Sore Throat, Ear Infections, Cramps, STDs, Strep Throat, Throat Infections, Feeding Problems For Newborns, Vomiting, Teething, Gastrointestinal Problems, Anxiety, Depression, Formula Advice For Newborns, Concussion, Head Injuries, Bone Fractures, Hair Loss, Alopecia, Eye Infections, Urinary Tract Infections, Constipation, Appendicitis, Pharyngitis, Medication Therapy Management etc. As can be appreciated, other or additional types of medical services and/or health care services can be provided. The medical services and/or health care services that can be provided can include, but are not limited to, 1) providing advice and/or recommendations about a medical condition, 2) diagnosing a medical condition, 3) providing referral services for a medical condition, 4) prescribing medicine for a medical condition, 5) periodically monitoring a medical condition, 6) providing routine check-up services, 7) providing advice and/or recommendations about medical and/or health matters, 8) providing a course of treatment for a medical condition, 8) providing health counseling, 9) providing health information, 10) providing wellness counseling, and/or 11) providing wellness information. As can be appreciated, other or additional services can be provided to the patient. In essence, any type of medical condition, medical concern, health concern, wellness concern, etc. can be addressed by the novel method for providing medical services of the present invention. Hereinafter, these services will be collectively referred to as medical services. As can be appreciated, the type of services provided to a patient will depend on the specific medical condition, medical concern, wellness concern, and/or health concern of the patient. In many instances, the medical provider will be able to diagnose, address and/or treat the specific medical condition, medical concern, wellness concern, health concern, etc. of the patient. In some instances, the specific medical condition, medical concern, wellness concern, health concern, etc. of the patient may be too complicated or complex to address via an audio and/or video link, thus the medical provider in such situations may have to refer the patient to a hospital, a doctor's office, counselor, psychiatrist/psychologist, medical specialist, health professional, dietician, rehabilitation facility, a traditional medical clinic for further counseling, treatment and/or diagnosis, or some other location or professional that can address the patient's needs and/or requirements.

In still another and/or alternative non-limiting aspect of the invention, the novel method of the present invention can include the use of a medical kiosk to enable the patient to conveniently communicate with the medical provider. One or more medical kiosks can be used in the present invention. Generally, a plurality of medical kiosks that are located at one or more locations are used in the method of the present invention; however, it can be appreciated that a single medical kiosk can be used in accordance with the present invention. Typically one or more medical providers provide services to one or more medical kiosks. The size, shape, configuration and look of the medical kiosk are non-limiting. In one non-limiting embodiment of the invention, the medical kiosk provides a private or semi-private environment for a patient to communicate with a medical provider that is located remotely from the medical kiosk. In one non-limiting arrangement, the medical kiosk includes an enclosure that is designed to enable a patient to enter the enclosure and communicate with the medical provider while in the enclosure. The size, shape and configuration of the enclosure of the medical kiosk are non-limiting. In another and/or alternative non-limiting arrangement, the medical kiosk includes one or more walls that form all or a portion of the enclosure. The enclosure may include one or more doors or entry points to enable a patient to enter and exit the enclosure. In another and/or alternative non-limiting arrangement, the medical kiosk includes a floor and/or a ceiling. The ceiling, when included, can include a portion that is partially or fully transparent; however, this is not required. In another and/or alternative non-limiting arrangement, the medical kiosk is modular in configuration to enable the medical kiosk to be set up in various configurations to enable the medical kiosk to be used in various types of spaces. The medical kiosk can be formed of any number of materials (e.g., plastic, foam, metal, wood, etc.). The walls of the medical kiosk can be designed to be interchangeable to enable the door, when used, to be positioned on various locations on the medical kiosk; however, this is not required. The medical kiosk can include a floor and/or ceiling to provide increased privacy for the patient when the patient is inside the room or cavity of the medical kiosk; however, this is not required. The medical kiosk can include a table, ledge, bench, and/or seat on the interior and/or exterior of the medical kiosk; however, this is not required. Such table, ledge, bench, and/or seat, when used, can be designed to be connected in multiple locations on the exterior and/or interior of the medical kiosk; however, this is not required. The modular configuration of the medical kiosk can be such that it can be easily assembled and disassembled so that the medical kiosk can be easily brought into a location and easily set up, or be easily removed from a location; however, this is not required.

In yet another and/or alternative non-limiting aspect of the invention, the novel method of the present invention can include the use of a medical kiosk that includes one or more data input terminals. The one or more data input terminals can be located on one or more locations on the exterior of the medical kiosk; however, this is not required. Alternatively, or additionally, the one or more data input terminals can be located on one or more locations in the interior or enclosure of the medical kiosk; however, this is not required. The one or more data input terminals can include a video display to display information regarding identification and/or data entry, a camera and/or video camera used to collect information for identification and/or data entry, a key pad or key board for identification and/or data entry, a touch screen for identification and/or data entry, microphone and voice recognition software for identification and/or data entry, fingerprint scanner for identification and/or data entry, retina scanner for identification and/or data entry, and/or face and/or body scanners for identification and/or data entry. As can be appreciated, other or additional devices can be included on the medical kiosk to display and/or obtain information regarding identification and/or data entry. The medical kiosk can be used by the patient to enter/convey basic information about the patient. Such information includes, but is not limited to, a) patient name, b) patient address, c) patient contact information (e.g., home address, work address, phone number, email address, pager number, work number, etc.), d) patient age, e) patient sex, f) patient height, g) patient weight, h) patient medical history, i) current medicines used by patient, j) reason (s) for visit by patient, k) patient current symptoms, l) patient insurance information, m) patient payment information, n) patient's current doctor, o) guardian or patent information, and/or p) next of kin information. As can be appreciated, other or additional information can be inputted/conveyed by the patient.

In still another and/or alternative non-limiting aspect of the invention, the novel method of the present invention can include a medial kiosk that can be designed to provide information to the patient prior to and/or during the inputting/conveying of information by the patient to the medical kiosk. In one non-limiting embodiment of the invention, the medical kiosk can include audio and/or visual instructions and/or displays used to provide a) information about the medical kiosk, b) how to use the medial kiosk, c) how to properly input/convey information to the medical kiosk, d) provide instructions and/or interactions with the patient during the inputting/conveying of information by the patient to the medical kiosk, e) the wait time for the patient's use of the medical kiosk, f) a list of patient's waiting to use the medical kiosk, and/or g) information regarding whether the medical kiosk is in use or is available. In another and/or alternative non-limiting embodiment of the invention, the medical kiosk can include light and/or sound indicators to provide information regarding whether the medical kiosk is in use or is available; however, this is not required. In still another and/or alternative non-limiting embodiment of the invention, the medical kiosk can include a notification system to a patient that the medical kiosk is available or will soon be available; however, this is not required. Such notification can be sent via email, phone, pager, internet, etc. Such notification system can be useful when the medical kiosk is not currently available to the patient. The patient can input the information into the medical kiosk and then go home, run other errands, etc., and then be later notified when the medical kiosk is available or will soon be available. The medical kiosk and/or notification system can also be used to inform the patient when and/or where other medical kiosks are available; however, this is not required. This service, when available, can be used to inform the patient that a nearby medical kiosk has a shorter wait period or is currently available, thus providing the patient with the option of traveling to another available medical kiosk instead of waiting for the current medical kiosk to become available; however, this is not required. This service, when available, can also be used to inform the patient when a prescription is ready for pickup and/or for conveying prescription information to the patient; however, this is not required. This service, when available, can also be used to inform the patient when a follow-up visit is due and/or scheduled; however, this is not required. As can be appreciated, the notification system can be used for other or additional services.

In yet another and/or alternative non-limiting aspect of the invention, one or more attendants can be used with the medical kiosk; however, this is not required. In one non-limiting embodiment of the invention, the medical kiosk can have one or more attendants assist a patient during the use of the medical kiosk (e.g., assist in check-in procedures, assist check-out procedures, assist in entering/exiting the medical kiosk, answering questions about the medical kiosk, assist in maintaining privacy/security of a patient while using the medical kiosk, assist user during payment of medical services, assist user in obtaining a prescription, etc.); however, this is not required. Such attendant, when used, can be a medical provider or non-medical provider. The one or more attendants, when used, can also or alternatively clean and/or sanitize various regions of the medical kiosk prior to and/or after being used by a patient and/or set up the medical kiosk for a new user; however, this is not required. For example, prior to and/or after one or more patients have entered the medical kiosk, the one or more attendants can clean/sanitize one or more exterior surfaces and/or regions of the medical kiosk (e.g., medical kiosk door, medical kiosk check-in terminal, medical kiosk desk top, medical kiosk exterior walls, medical kiosk touch screen, medical kiosk monitors, seating/tables in waiting area near medical kiosk, etc.); however, this is not required. In an another and/or additional example, prior to and/or after one or more patients have entered the medical kiosk, the one or more attendants can clean/sanitize one or more interior surfaces of the medical kiosk (e.g., medical kiosk door, medical kiosk floor, medical kiosk bench, medical kiosk chair, medical kiosk user terminal, medical kiosk interior desk top, medical kiosk interior walls, medical kiosk touch screen, medical kiosk monitors, medical kiosk instrument doors, medical devices/instruments used by and/or touched by user when in the medical kiosk, any other surface in the interior of the medical kiosk, etc.); however, this is not required. In still another and/or additional example, prior to and/or after one or more patients have entered the medical kiosk, the one or more attendants can set up the medical kiosk for a user (e.g., clean/sanitize interior surfaces of medical kiosk; clean/sanitize medical devices/instruments used and/or touched by a prior user; reposition medical devices/instruments into device storage areas; replace disposable components on medical devices/instruments; replenish paper in a printer; clear a paper jam in a printer; replace batteries for one or more electronic components; close medical device/instrument compartments doors in the medical kiosk; reset user touch screen for next user in the medical kiosk; fix, repair and/or replace non-operating, damaged or broken medical devices/instruments in the medical kiosk; fix, repair and/or replace electronic components, computers, fans, light bulbs, UV bulbs, UV devices, etc. in the interior and/or exterior of the medical kiosk; refill cleaning and/or sanitizing fluid; etc.); however, this is not required. In yet another and/or additional example, the one or more attendants can be used to assist one or more users in the medical kiosk. Generally, such assistance will occur only after requested by the user in the medical kiosk or by the medical provider that is assisting the user while in the medical kiosk; however, this is not required. For instance, the one or more attendants can assist a user in the medical kiosk if the one or more attendants hear a verbal request from the user, receive notice (e.g., light indicator activated by user, sound indicator activated by user, hear user talking via a speaker to attendant, hear user talking through walls of medical kiosk, receive a notice from the medical provider [e.g., phone call, email, light indicator, etc.], etc.); however, this is not required.

In still yet another and/or alternative non-limiting aspect of the invention, the medical kiosk can include a sanitizing system (e.g., UV system, mist system, etc.) that can be automatically activated and/or activated by the attendant prior to and/or after a patient has used the medical kiosk; however, this is not required.

In another and/or alternative non-limiting aspect of the invention, the medical kiosk can be made of one or more materials that resist or prevent the growth of bacteria, viruses and/or other micro-organisms; however, this is not required. In one non-limiting embodiment, the floor, walls and ceiling of the medical kiosk include or are fully made of materials that resist or prevent the growth of bacteria, viruses and/or other micro-organisms; however, this is not required.

In yet another and/or alternative non-limiting aspect of the invention, the novel method of the present invention can include a medical kiosk that includes a payment center that enables a user to pay for medical services, prescriptions, medical equipment, medical accessories, etc. prior to and/or after the user uses the medical kiosk; however, this is not required. The payment center can be in any form (e.g., credit card reader, mobile phone scanner, transmitter/receiver device, electronic scanner, cash receiver, etc.). The payment center may include a touch pad, key board, scanner, receiver, transmitter, credit card/debit card or some other card reader, smart phone or other smart device reader/scanner, finger and/or, eye scanner, monitor, chair, table, shelf, printer, instructions on how to use the payment center, etc. The payment center can be located on the exterior and/or interior of the medical kiosk. Generally, the user is required to register and pay for the medical services prior to obtaining medical services from the medical provider; however, this is not required. In one non-limiting arrangement, the medical kiosk includes a registration station on the exterior of the medical kiosk (e.g., exterior wall of the medical kiosk, on a table exterior to the medical kiosk, etc.); however, this is not required. As can be appreciated, a user can be allowed to wirelessly connect to the medical kiosk or to some other computer network so as to wirelessly register and/or enter payment information for use of the medical kiosk; however, this is not required. In such an arrangement, a user could register to use a medical kiosk, enter in payment for use of the medical kiosk, set an appointment time for use of the medical kiosk, select a particular medical kiosk to use at some particular location, etc. at some location near or remote from the medical kiosk via a smart phone or other smart device, a computer, etc.

In yet another and/or alternative non-limiting aspect of the invention, the novel method of the present invention can include a medical kiosk that includes an interior cavity or room that provides privacy to the patient when inputting and/or conveying data to the medical kiosk, and/or communicating with a medical provider via an audio and/or video link. The size, configuration and/or arrangement of the interior cavity or room are non-limiting. The interior cavity or room can include a) one or more speakers, b) one or more microphones, c) one or more video displays, d) data input device, e) one or more chairs and/or other types of seating areas, f) one or more tables, g) one or more doors, h) one or more shelves, i) one or more compartments used to contain medical supplies, medical instruments, etc., j) one or more light switches, k) one or more power outlets, l) sterilization system, and/or m) one or more lights. As can be appreciated, the interior cavity or room can include other or additional items. The size and configuration of the interior cavity or room can be designed to enable wheelchair access and maneuvering inside the interior cavity or room; however, this is not required. For example, the interior cavity or room can be designed to enable a standard wheelchair to move 90°, 180° and/or 360° while in the medical kiosk. The size and configuration of the interior cavity or room can be designed to provide sufficient room for the patient so that the patient can easily move within the interior cavity or room and/or the patient does not feel cramped or claustrophobic when in the interior cavity or room; however, this is not required.

In another and/or alternative non-limiting aspect of the invention, the novel method of the present invention, the method for providing medical services in accordance with the present invention is designed to provide a convenient and low-cost structure (e.g., medical kiosk) that can be placed in many different locations, and which enable patients to conveniently access and obtain medical advice and/or care. Medical providers that are located locally or throughout the world can be used to communicate with the patient accessing the medical kiosk. As such, the medical services can be offered year around and at all times so long as there is a qualified medical provider somewhere in the world that is available and is qualified to provide medical assistance via the medical kiosk. Such an arrangement can be more convenient to the medical provider since the medical provider can work from home or from some other convenient location. The arrangement is also convenient to the patient since the patient can access medical assistance via the medical kiosk at the time and place of choosing. Indeed, in rural areas or smaller communities that do not have a local hospital or local doctor's offices nearby, the installation of a medical kiosk in the local drug store, department store, grocery store, etc., results in more accessible and timely medical care for patients in such communities. The costs associated with providing medical care via the medical kiosk may be less than if the patient seeks medical assistance from a hospital, clinic or doctor's office, thus resulting in the patient potentially saving money. As can be appreciated, other or additional advantages may exist by the method of the present invention.

It is one non-limiting object of the invention to provide tele-med services that are convenient to a user.

It is another and/or alternative one non-limiting object of the invention to provide tele-med services that are cost effective to a user.

It is still another and/or alternative one non-limiting object of the invention to provide tele-med services that can be provided to a user via a medical kiosk.

It is yet another and/or alternative one non-limiting object of the invention to provide tele-med services that can be provided to a user via a modular medical kiosk.

It is still yet another and/or alternative one non-limiting object of the invention to provide a medical kiosk that is easy to assemble and disassemble.

It is another and/or alternative one non-limiting object of the invention to provide a medical kiosk that includes an easy and convenient registration system and payment system.

It is still another and/or alternative one non-limiting object of the invention to provide a medical kiosk that provides privacy to a user when obtaining medical services.

It is yet another and/or alternative one non-limiting object of the invention to provide a medical kiosk that sized and shaped to accommodate disabled or handicapped users.

It is still yet another and/or alternative one non-limiting object of the invention to provide a medical kiosk that includes medical instruments that can be used by a user when obtaining medical services.

It is another and/or alternative one non-limiting object of the invention to provide a medical kiosk that includes video conferencing capabilities between a user and a medical provider.

It is still another and/or alternative one non-limiting object of the invention to provide a medical kiosk that provides the option to play back one or more portions of the video conference session to the user after the video conference between the user and medical provider has been completed.

These and other objects and advantages will become apparent to those skilled in the art upon reading and following the description taken together with the accompanying drawings.

BRIEF DESCRIPTION OF THE DRAWINGS

Reference may now be made to the drawings which illustrate various preferred embodiments that the invention may take in physical form and in certain parts and arrangement of parts wherein.

DETAILED DESCRIPTION OF ONE NON-LIMITING EMBODIMENT

Figure 1:
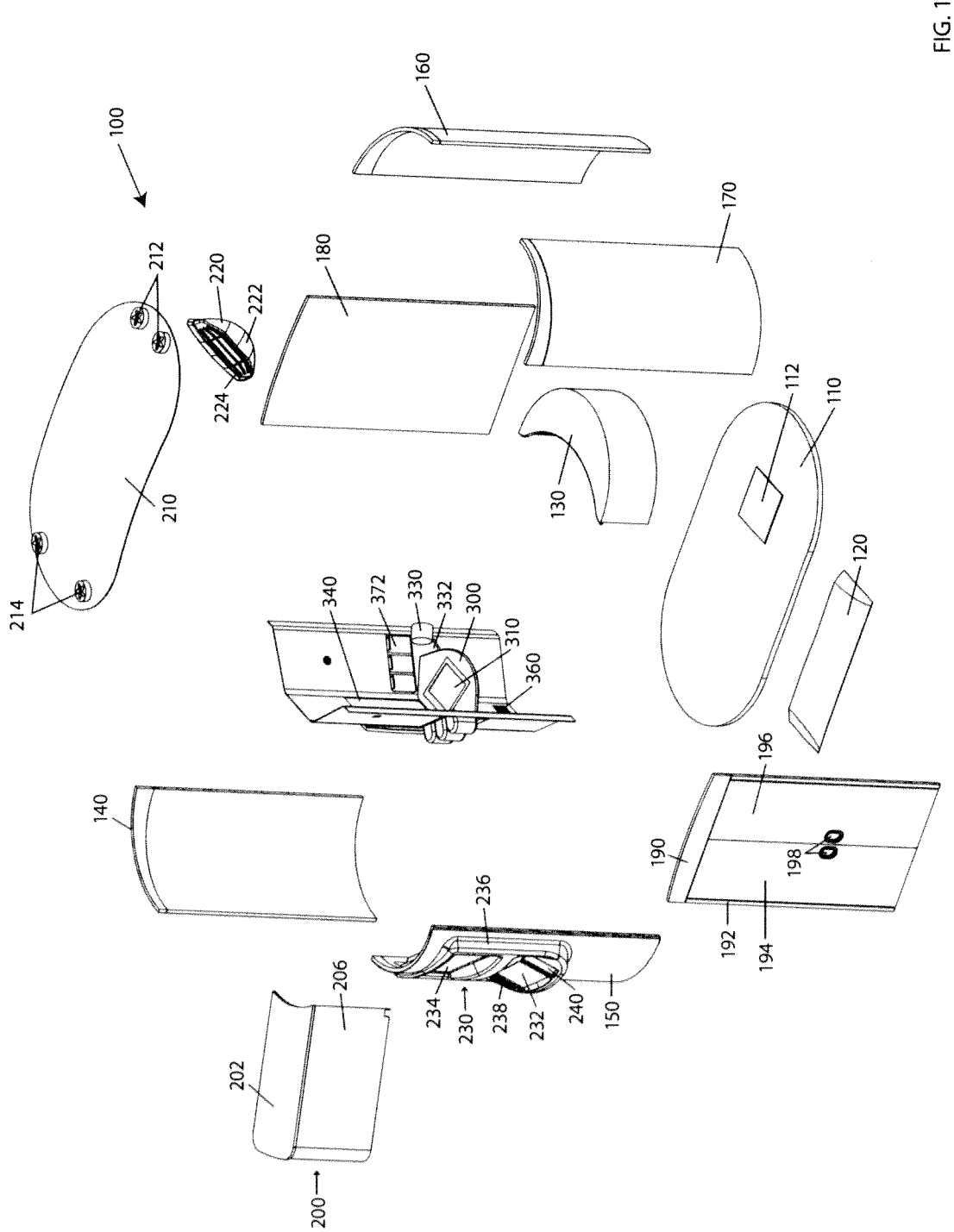
FIG. 1 is an exploded view of a medical kiosk in accordance with the present invention.

Referring now to the drawings wherein the showings are for the purpose of illustrating one non-limiting embodiment of the invention only and not for the purpose of limiting same, FIGS. 1-11 illustrate one non-limiting embodiment of the medical kiosk in accordance with the present invention. The medical kiosk 100 is designed to be used by a user to obtain medical services. Such medical services are generally tele-med services wherein one or more medical providers located at a remote location provide medical services to one or more users that are using the medical kiosk. As can be appreciated, non-tele-med services can also be provided to a user that is using the medical kiosk.

The shape, size and configuration of the medical kiosk are non-limiting. The materials and colors of the medical kiosk are also non-limiting. Generally, the materials used to form the medical kiosk include materials that resist or prevent microbial growth; however, this is not required. The medical kiosk illustrated in FIGS. 1-11 is designed to accommodate about 1-4 adults; however, it can be appreciated that the medical kiosk can be designed to accommodate additional users.

The medical kiosk is generally designed to be modular so that it can be easily assembled and disassembled; however, this is not required. FIG. 1 illustrates one non-limiting set of modular components of the medical kiosk. The medical kiosk generally includes a floor panel 110; however, this is not required. The floor panel, when used, is generally a one piece unit; however, the floor panel can be formed of multiple pieces. The floor panel is generally formed of a durable material (e.g., plastic, metal, wood, composite material, man-made materials, etc.). The floor panel can be formed of a slightly compressible material to facilitate in the comfort of walking on the floor panel; however, this is not required. The floor panel is illustrated as having an oval shape; however, other shapes can be used (e.g., circular, square, rectangular, polygonal, etc.). The maximum length of the floor panel is generally 3-15 feet, typically 4-12 feet, more typically about 6-10 feet, and even more typically about 8-9 feet; however, other lengths can be used. The maximum width of the floor panel is generally 3-10 feet, typically 4-8 feet, and more typically about 4-6 feet; however; other widths can be used. The top surface area of the floor panel is generally 10-150 sq. ft., typically 15-80 sq. ft., and more typically about 50-60 sq. ft.; however, other surface areas of the floor panel can be used. The floor panel can be sized to enable a user in a wheelchair to enter the medical kiosk and turn and/or fully maneuver in the medical kiosk while sitting in the wheelchair; however, this is not required. The thickness of the floor panel is generally about 0.1-5 inches, and typically about 0.25-3 inches; however, other thicknesses of the floor panel can be used.

A weight scale 112 can optionally be partially or fully embedded in the floor panel. As can be appreciated, a weight scale can be placed on the top surface of the floor panel and/or positioned on other regions of the medical kiosk (e.g., chair, bench, etc.). The weight scale, when used, provides information about the weight of a user. The information from the scale can be electronically (e.g., wired, wirelessly) transferred to a medical provider and/or displayed to the user and/or medical provider.

A ramp 120 can be optionally used to facilitate entry and exiting of the medical kiosk; however, this is not required. The shape and size of the ramp are non-limiting. The ramp can be made of a similar material as the floor panel; however, this is not required. The ramp generally includes a sloped surface to facilitate in transitioning from a floor surface to the top surface of the floor panel; however, this is not required.

The medical kiosk can optionally include one or more benches 130, stools and/or chairs. When bench 130 is included in the medical kiosk, the bench is generally positioned on the back interior wall of the medical kiosk; however, this is not required. The bench can be used to allow a parent, guardian, spouse, relative, friend, etc. to sit in the medical kiosk while the user is obtaining medical services in the medical kiosk. The bench can be designed to enable one or more persons to sit on the bench. The bench can optionally include a storage space 132 under the seat of the bench that can be used to store supplies, equipment, etc. for the medical kiosk. A liftable seat section 134 can be used to access the storage space. When the bench includes a storage space, the bench can include a lock to limit access to the storage space; however, this is not required. As can be appreciated, the medical kiosk can include one or more chairs, not shown, to enable one or more users to sit in the medical kiosk while receiving medical services in the medical kiosk. The bench is generally about 10-25 inches high, and typically about 16-20 inches high; however, other heights can be used.

Figure 3:
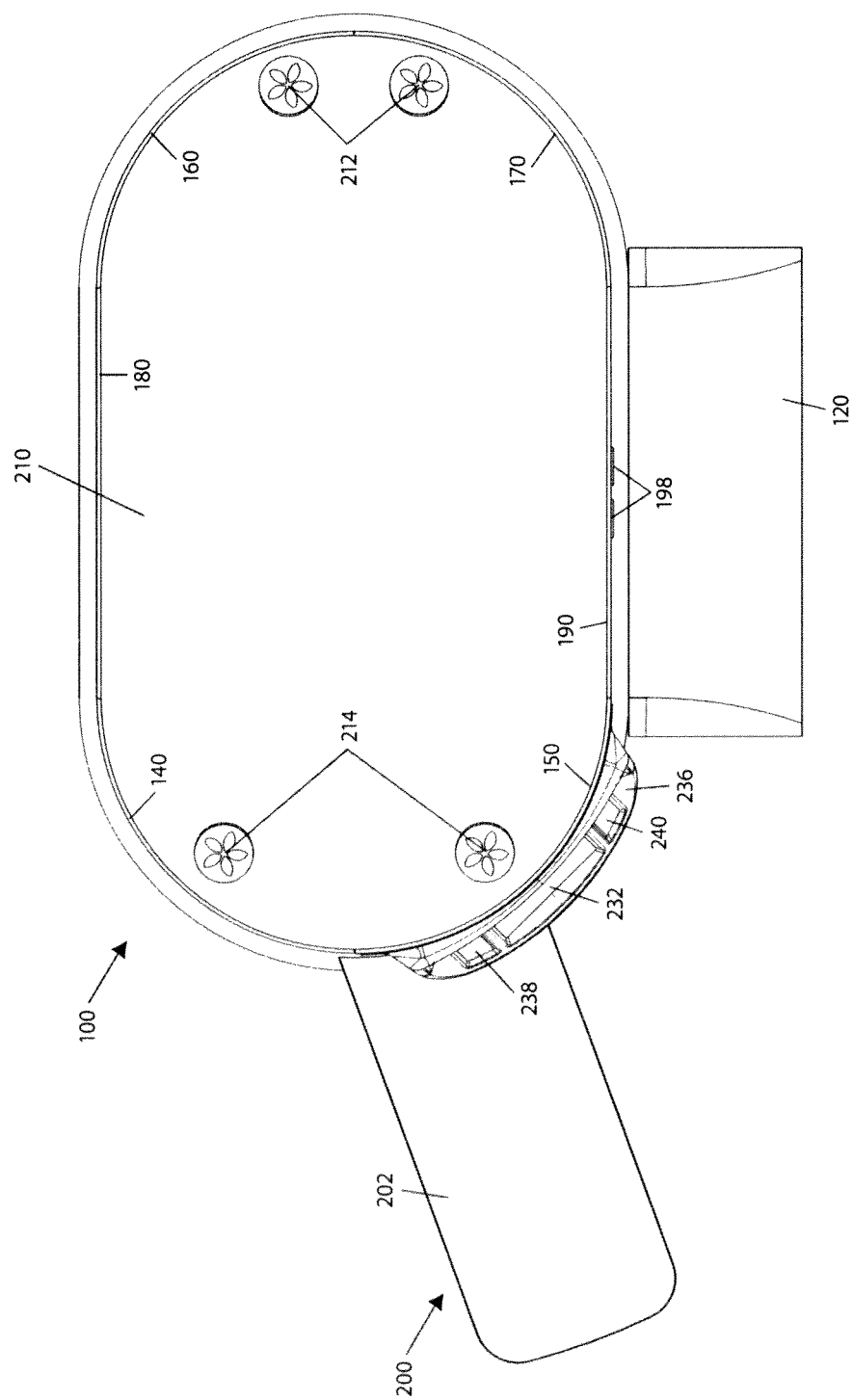
FIG. 3 is a top view of the medical kiosk of FIG. 1.
Figure 4:
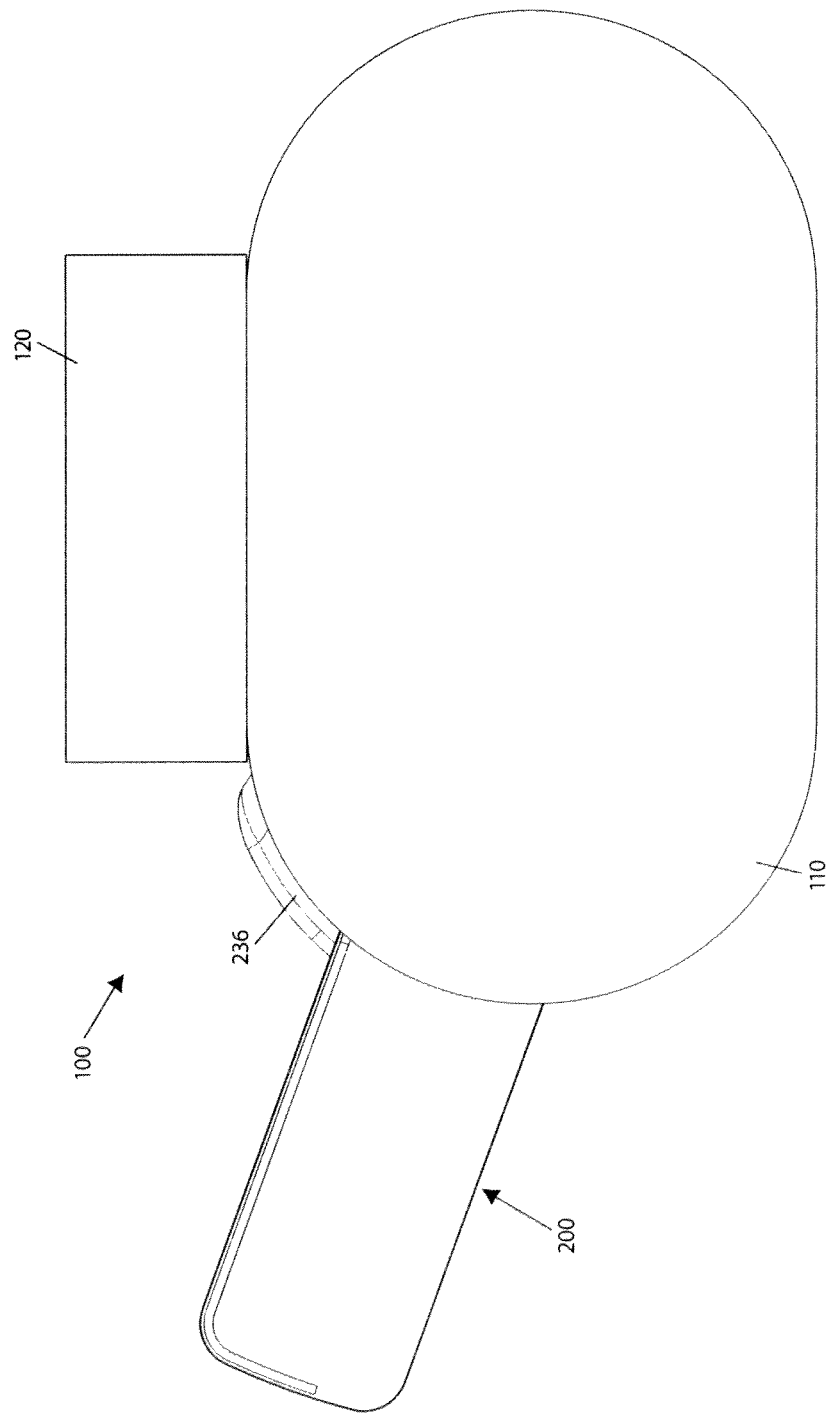
FIG. 4 is a bottom view of the medical kiosk of FIG. 1.
Figure 8:
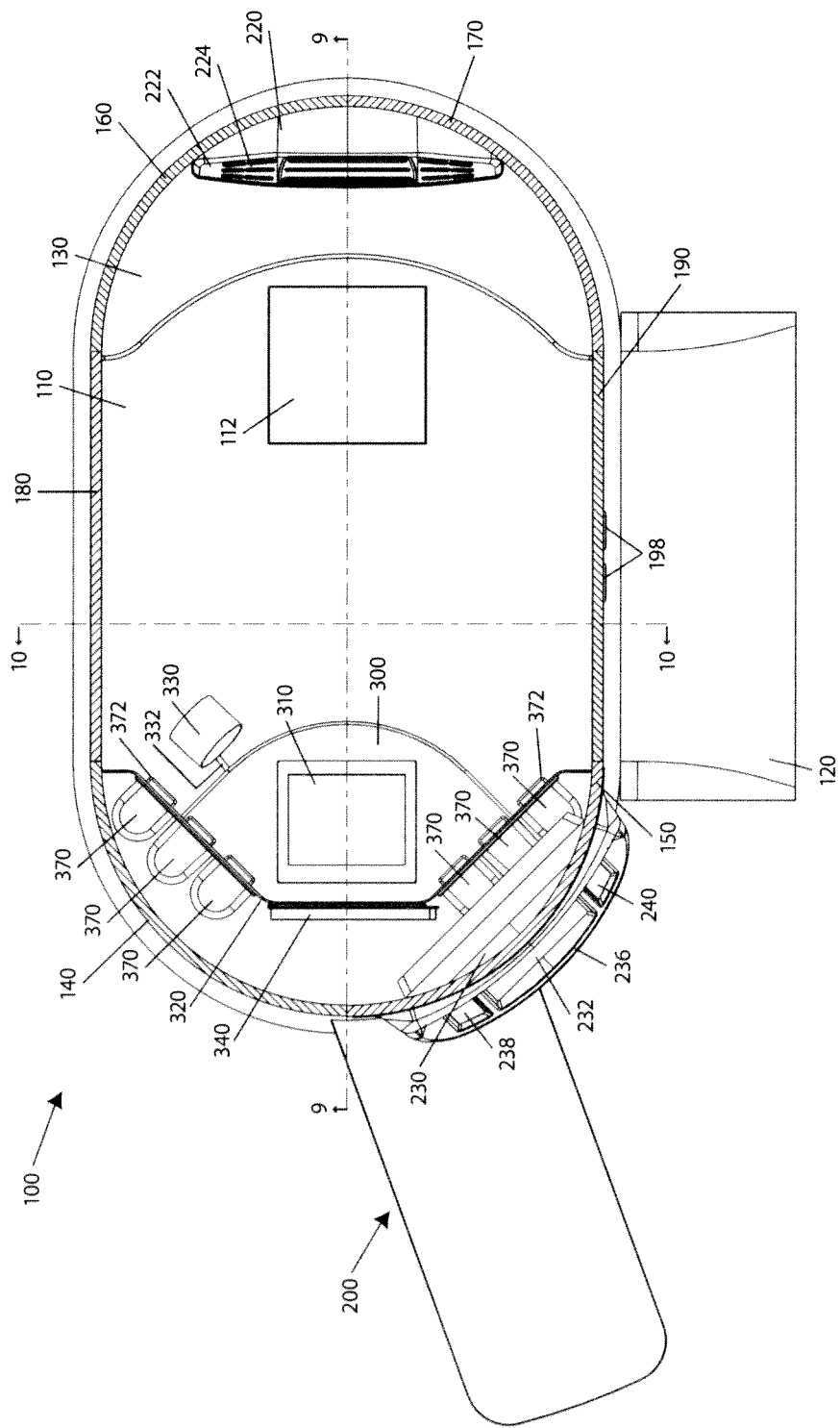
FIG. 8 is a top interior view of the medical kiosk of FIG. 1.

The medical kiosk is illustrated as having two front panels 140, 150, two rear panels 160, 170, one side wall 180, and one door system 190. The front panels, rear panels, side wall, and door system are generally formed of a durable material (e.g., plastic, metal, wood, composite material, man-made materials, etc.). As can be appreciated, the medical kiosk can be designed to only include a single front panel and/or a single rear panel. As can also be appreciated, the medical kiosk can be designed to include more than two front panels and/or more than two rear panels. As can be appreciated, the medical kiosk can be designed to include more than one side wall and/or more than one door system. As can also be appreciated, a side wall can be substituted for another door system; however, this is not required. The general shape and size of the front and rear panels are the same; however, this is not required. As illustrated in FIG. 1, the shape of the front and rear panels is arcuate. The radius of curvature is about 10-100 inches, typically 15-50 inches, and more typically about 20-35 inches; however, other radius of curvatures can be used. As illustrated in FIGS. 1 and 3, the front and rear panels have an angle of curvature of about 90° or a quarter of a circle; however, it can be appreciated that one or both rear and/or front panels can have different angles of curvature. The general shape and size of the side wall and the door system are generally the same; however, this is not required. As illustrated in FIGS. 1 and 3, the side wall and door system lie in a generally flat plane; however, this is not required. As illustrated in FIG. 8, the assembly of the front and rear panels and the side wall and door system forms a generally oval shape for the medical kiosk. The two front panels and two rear panels are illustrated as having the same or similar footprint. Likewise, the side wall and the door system have the same or similar footprint. The similarity in the shape and footprint of the wall components of the medical kiosk enables the medical kiosk to be assembled in a manner that is convenient for the facility that will include the medical kiosk. For example, if the door system needs to be positioned on the left side of the medical kiosk, instead of the right side, the similarly shaped side wall and door system enables the medical kiosk to be assembled in such a manner. Also, if the registration station of the medical system needs to be placed on the left side or right side or on the rear end of the medical kiosk instead of the front end, the similarly shaped front and rear panels can be easily exchanged to create such configuration for the medical kiosk. The modular medical kiosk not only accommodates multiple configurations of the medical kiosk, it also facilities in enabling the medical kiosk to be moved into an existing facility and then assembling the medical kiosk in such facility without having to modifying the entry ways into or out of the facility. The thickness and height of the front panels, rear panels, side wall and door system are non-limiting. Generally, the maximum height of the front panels, rear panels, side wall and door system is about 5-12 ft., typically about 6-9 ft., and more typically about 7-8 ft.; however, other heights can be used. The thickness of the front panels, rear panels, side wall and door system is generally about 0.5-10 inches, typically about 1-5 inches, and more typically about 1-2 inches; however, other thicknesses can be used. The front panels, rear panels, side wall and door system can optionally include insulation, sound dampening material, etc.; however, this is not required. The front panels, rear panels, side wall and door system can be designed to be connected together in a variety of ways (e.g., bolted/screwed together, latched together, snap fitted together, press fitted together, etc.). Generally, the arrangement is used to connect together the front panels, rear panels, side wall and door system is selected to enable easy connecting and disconnecting of the front panels, rear panels, side wall and door system from one another. One or more of the front panels, rear panels, side wall and door system can include openings, windows, transparent/semi-transparent regions that allow for ventilation, illumination, and/or viewing; however, this is not required. Generally, front panels, rear panels, side wall and door system are mostly or fully formed of opaque or non-transparent materials so as to ensure the privacy of the user in the medical kiosk; however, this is not required.

Figure 2:
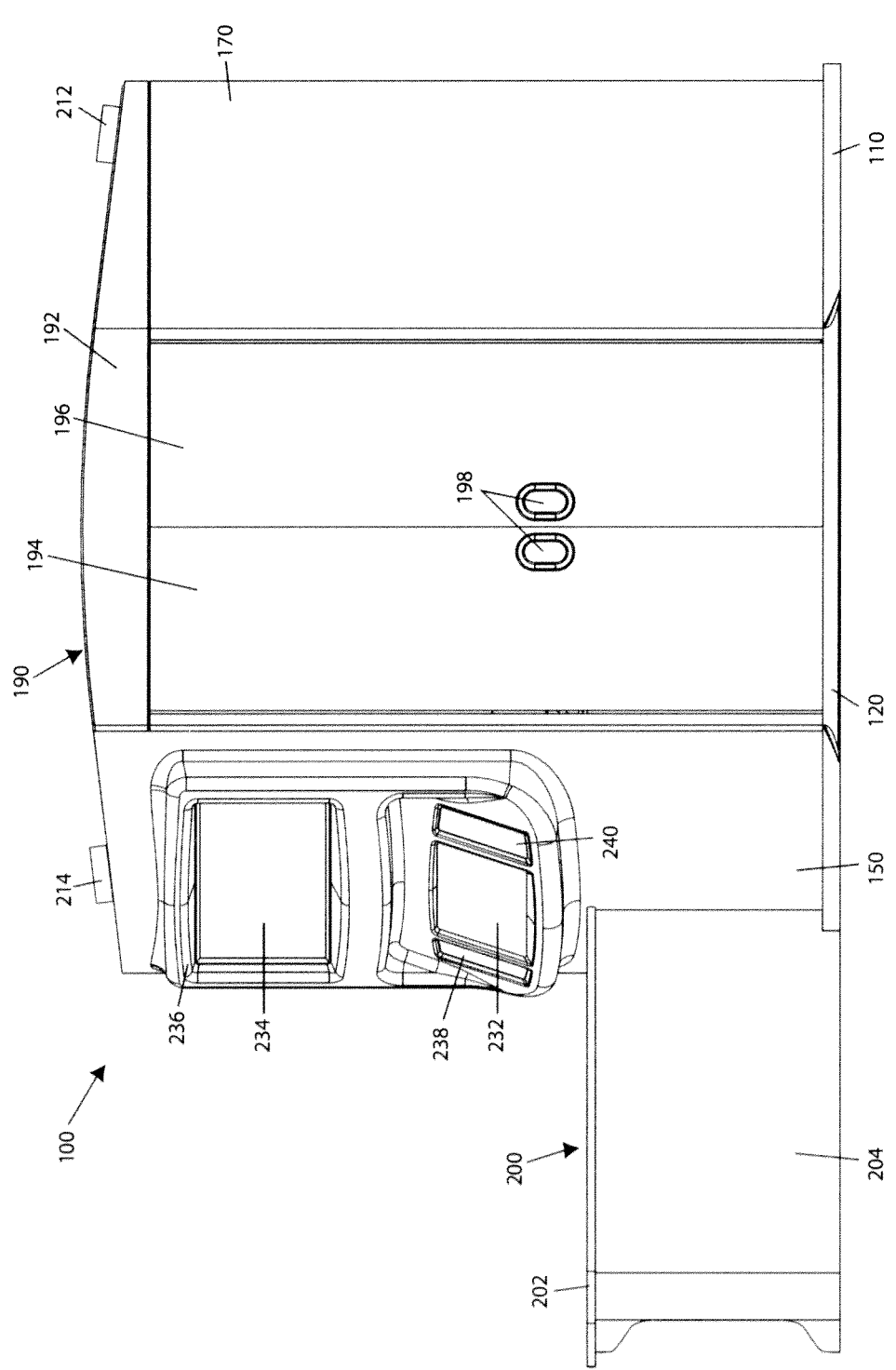
FIG. 2 is a side view of the medical kiosk of FIG. 1.

The configuration of the door system 190 is non-limiting. As illustrated in FIGS. 1 and 2, the door system includes a frame 192 and two doors 194, 196; however, it can be appreciated that the door system only includes a single door. Each door includes a handle or grasp cavity 198 on one or both sides of the one or both doors. The one or more doors can be designed to open and close in a variety of ways (e.g., swing open and closed, slide open and closed on a top/bottom rail system, etc.). As can be appreciated, the one or more doors for the medical kiosk can also or alternatively be positioned on one or more of the front or rear panels; however, this is not required. The maximum height of the doors is generally about 5-9 ft., and typically about 6-7 ft.; however, other heights can be used. The maximum width of the entry provided by the one or more doors when fully open is generally about 15-60 inches, typically about 25-55 inches, and more typically about 30-50 inches; however, other widths can be used. The door opening is generally selected to enable a standard wheelchair to pass through the opening; however, this is not required. The door system can optionally include an indicator (e.g., light, message, etc.) that indicates when the medical kiosk is in use or is available. As can be appreciated, the use indicator can be located on other or additional locations on the medical kiosk. The door system can optionally include a lock arrangement. The configuration of the lock arrangement is non-limiting. The lock arrangement, when used, can be designed to enable the user to lock the doors to the kiosk medical to prevent access to the interior of the medical kiosk while the user is in the medical kiosk; however, this is not required. The lock arrangement can also or alternatively be used to lock and prevent access to the interior of the medical kiosk when the medical kiosk is not in use; however, this is not required.

The medical kiosk can optionally include an exterior attendant station that is connected to and/or positioned near the medical kiosk. The exterior attendant station can be used by one or more attendants, medical providers, etc. As illustrated in FIGS. 1-5, 7 and 8, a desk 200 can be connected to and/or positioned next to an exterior wall of the medical kiosk. The desk can be formed of one or more pieces. When the desk is designed to be connected to an exterior wall of the medical kiosk, such connection arrangement is not limited (e.g., screw, bolt, clamp, press fit, snap arrangement, etc.). The desk can include a desk top 202, one or more legs, one or more shelf regions 206, one or more drawers, etc. One or more chairs, not shown, can be used to allow one or more attendants, medical providers, etc. to sit at the desk. The one or more one or more attendants, medical providers, etc. located at the desk can assist a user in using the medical kiosk, maintain and/or clean the medical kiosk, provide medical services to a user of the medical kiosk, etc. The desk is illustrated as positioned at or adjacent to one or both front panels; however, this is not required. Generally the attendant, when used, is not a medical provider. The attendant, when used, is generally trained to assist a user to use the medical kiosk; however, this is not required. The attendant can 1) provide assistance to a user during the registration process and/or payment process, 2) provide assistance to a user about the medical kiosk and how to use the medical kiosk, 3) provide assistance to a user regarding technology in the medical kiosk and how to use such technology in the medical kiosk, 4) provide assistance to a user to enter and/or exit the medical kiosk, 5) clean and/or sanitize the medical kiosk, and/or 6) answer and/or assist the user in other ways regarding the medical kiosk and/or services provided by the medical kiosk.

The medical kiosk can optionally include a ceiling panel 210. The ceiling panel can be formed of one or more pieces. The ceiling panel can be formed of a transparent or semi-transparent material to allow light to enter and illuminate the interior of the medical kiosk; however, this is not required. One or more lights, not shown, can be positioned on the ceiling panel to illuminate the interior of the medical kiosk; however, this is not required. The ceiling panel is illustrated as including four fan systems that are used to circulate air inside the medical kiosk. As can be appreciated, the location of the one or more fan systems on the ceiling panel is non-limiting. As can also be appreciated, more than or less than four fan systems can be positioned on the ceiling panel. As can also be appreciated, one or more fan systems can also or alternatively be positioned on other components of the medical kiosk (e.g., front panel, back panel, side wall, door system, floor panel, etc.). Generally, the rear fan systems 212 are designed to draw air into the medical kiosk and front fan systems 214 are designed to expel air out of the medical kiosk; however, this is not required. One or more fans systems can optionally include a filter system, to partially or fully filter dust, mites, airborne particles, micro-organisms, viruses, etc. from the air prior to the air entering into the medical kiosk and/or prior to the air exiting the medical kiosk; however, this is not required. The filter can include many different arrangements (e.g., HEPA filter, electronic filter, liquid filter, etc.).

The medical kiosk can optionally include a cleaning system that is designed to clean the interior of the medical kiosk and/or kill/neutralize some or all germs and/or other microorganisms in the medical kiosk. One non-limiting cleaning system that can be used is a UV sanitizing system 220. As can also be appreciated, a mist sanitizer can also or alternatively be used to fully or partially clean/sanitize one or more portions of the medical kiosk. As illustrated in FIGS. 1, 8, 9 and 11, the UV sanitizing system 220 can be connected to or positioned adjacent to the ceiling panel and rear panels; however, this is not required. The UV sanitizing system generally includes one or more UV lights that are designed to kill some or all of the germs and/or other micro-organisms in the medical kiosk. Generally the germs and/or other micro-organisms in the medical kiosk are treated when the interior of the medical kiosk does not include a user. The UV sanitizing system can optionally include one or more standard lights that can be used to provide illumination in the medical kiosk; however, this is not required. The UV sanitizing system can optionally include one or more vents that allow air drawn into the medical kiosk by fan systems 212 to flow into the interior of the medical kiosk; however, this is not required. The UV sanitizing system can optionally include a cooling fan for the one or more UV lights and/or optional standard lights; however, this is not required. The UV sanitizing system can optionally include all or a portion of a mist sanitizing system; however, this is not required. The UV sanitizing system can house one or more cameras, speakers, sensors (e.g., temperature sensor, motion sensor, sound sensor, etc.), etc. for use in the medical kiosk; however, this is not required. The UV sanitizing system includes a shroud 222 that includes vent/light openings 224 to house the components of the UV sanitizing system. The shape, size and configuration of the shroud are non-limiting. When a mist sanitizing system is additionally or alternatively used, one or more mist nozzles can be located in one or more regions of the medical kiosk so as to direct the sanitizing mist to desired locations in the medical kiosk. The sanitizing system, when used, can be activated by an attendant and/or a medical provider while the medical kiosk is not being used by a user. The doors to the medical kiosk can be closed and/or locked to prevent a user from entering the medical kiosk during a sanitizing process; however, this is not required.

Figure 5:
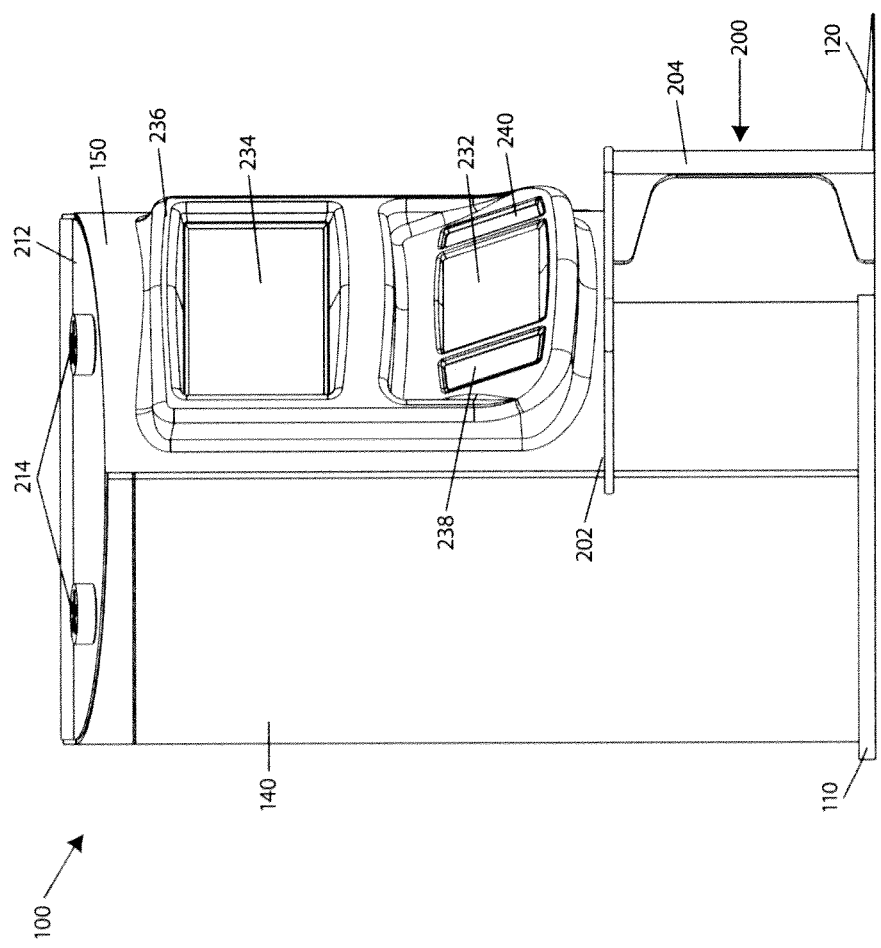
FIG. 5 is a front view of the medical kiosk of FIG. 1.
Figure 6:
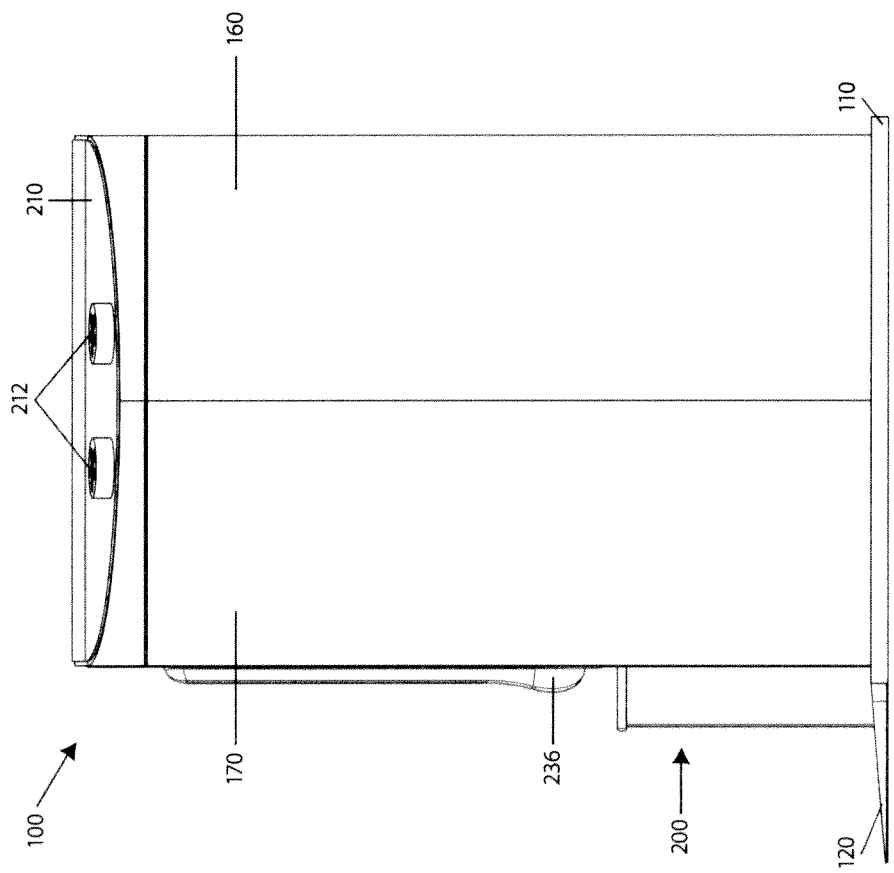
FIG. 6 is a rear view of the medical kiosk of FIG. 1.
Figure 7:
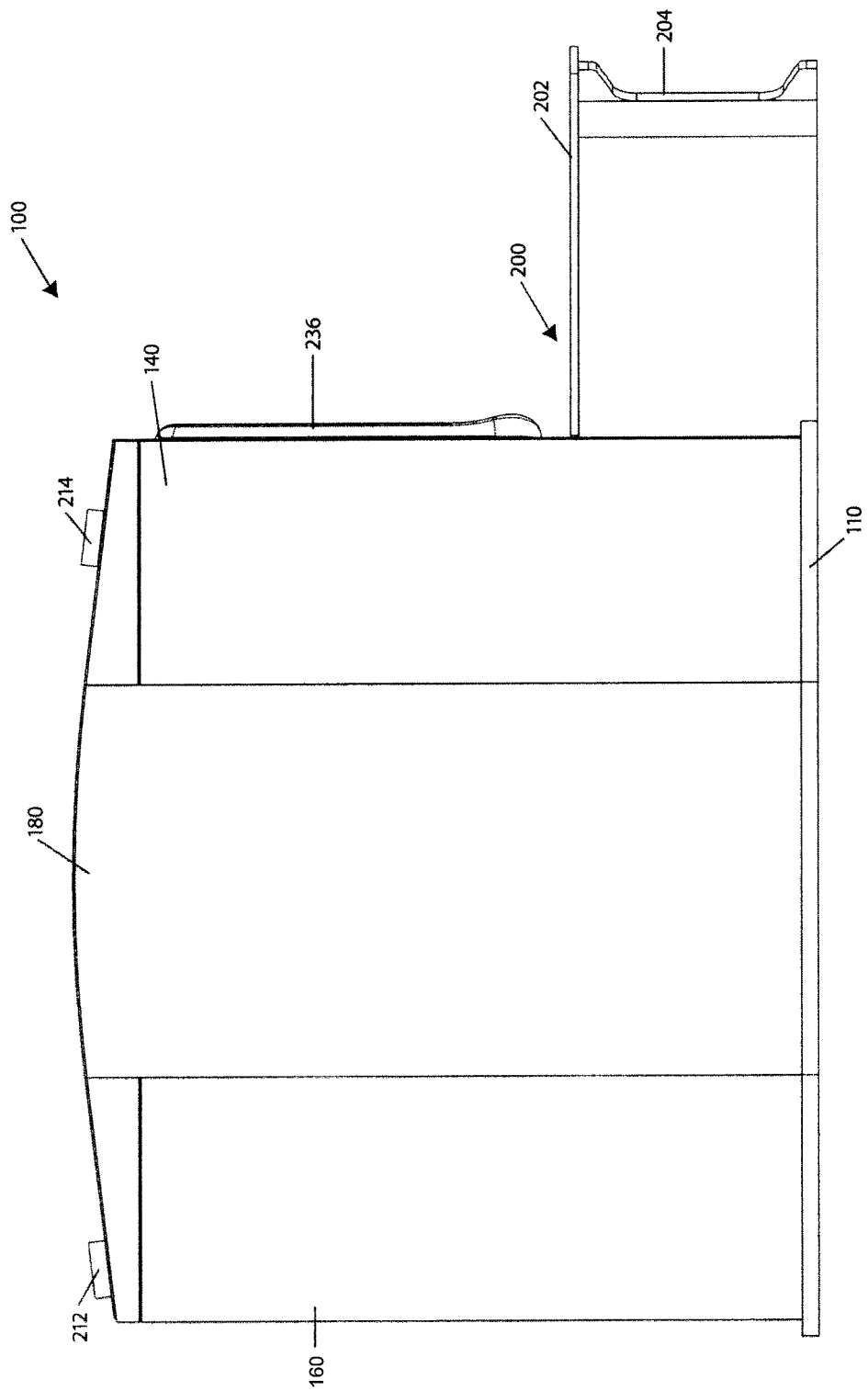
FIG. 7 is a side view of the medical kiosk of FIG. 1.

Referring now to FIGS. 1-3, 5 and 8, front panel 150 includes a registration station 230. The registration station is illustrated as including a touch screen 232, a display screen 234, and an optional frame 236 that such components can be mounted thereto. The shape of the frame, when used, is non-limiting. The frame, when used, can be designed to be easily removed from the front panel to enable servicing, repair, replacement, etc. of one or more components of the registration station; however, this is not required. As can be appreciated, the registration station can also or alternatively include other or optional features (e.g., additional display screen, additional touch screen, lights, buttons, switches, camera, speakers, microphone, keyboard, scanner, receiver, transmitter, credit card/debit card or other some other card reader, smart phone or other smart device reader/scanner, finger and/or eye scanner, shelf, printer, storage cavity, service access door, motion sensor, sound sensor, temperature sensor, logos, etc.). The touch screen is generally used to allow a user to enter in information about the user (e.g., age, sex, contact information, payment information, medical history, medical issue, etc.). The touch screen can be substituted for a keyboard; however, this not required. The frame is designed to mount the touch screen at some angle (e.g., 10-80°) relative to the front plane of the front panel 150 as illustrated in FIGS. 1, 2 and 5; however, this is not required. The frame optionally includes one or more side sections 238, 240 that can include one or more other or optional features of the registration station. As can be appreciated, one or more other or optional features of the registration station can also or alternatively be located on other regions of the registration station. The touch screen can display various types of information (e.g., electronic keyboard, instructions on how to register, questions that are displayed during registration, instructions during registration, information displayed to user during registration, various templates, various menus, various lists of information, etc.). As can be appreciated, the medical kiosk can be designed to accept voice commands during the registration process; however, this is not required. The display screen can be used to provide various types of information (e.g., registration information, information input by the user, advertising information, information about the medical kiosk, information about wait time for a medical kiosk, information as to the order of users waiting to use the medical kiosk, information about whether a medical kiosk is available or in use, cable TV, satellite TV, local broadcast TV, infomercial, medical programs, DVD materials, Blu-ray materials, etc.). Generally, a user enters payment information at the registration station (e.g., swipes a credit or debit card, etc.); however, it can be appreciated that payment information can also or alternatively be entered inside the medical kiosk, at the optional attendant station, wirelessly or over a network via a smart phone or other device or by a computer connected to a network, etc. If an attendant is available, the attendant can assist a user during the registration process; however, this is not required. Generally, the medical kiosk includes a single registration station; however, this is not required. As can be appreciated, the registration station can alternatively be located inside the medical kiosk, at the attendant station, on other panels or sidewalls of the medical kiosk, or located remotely from the medical kiosk (e.g., central registration center for use with multiple medical kiosks, etc.).

Referring now to FIGS. 1 and 8-11, a non-limiting interior of the medical kiosk is illustrated. As previously discussed, the interior room or cavity of the medical kiosk can optionally include a scale 112, a bench 130 and/or a UV sanitizing system 220.

Figure 9:
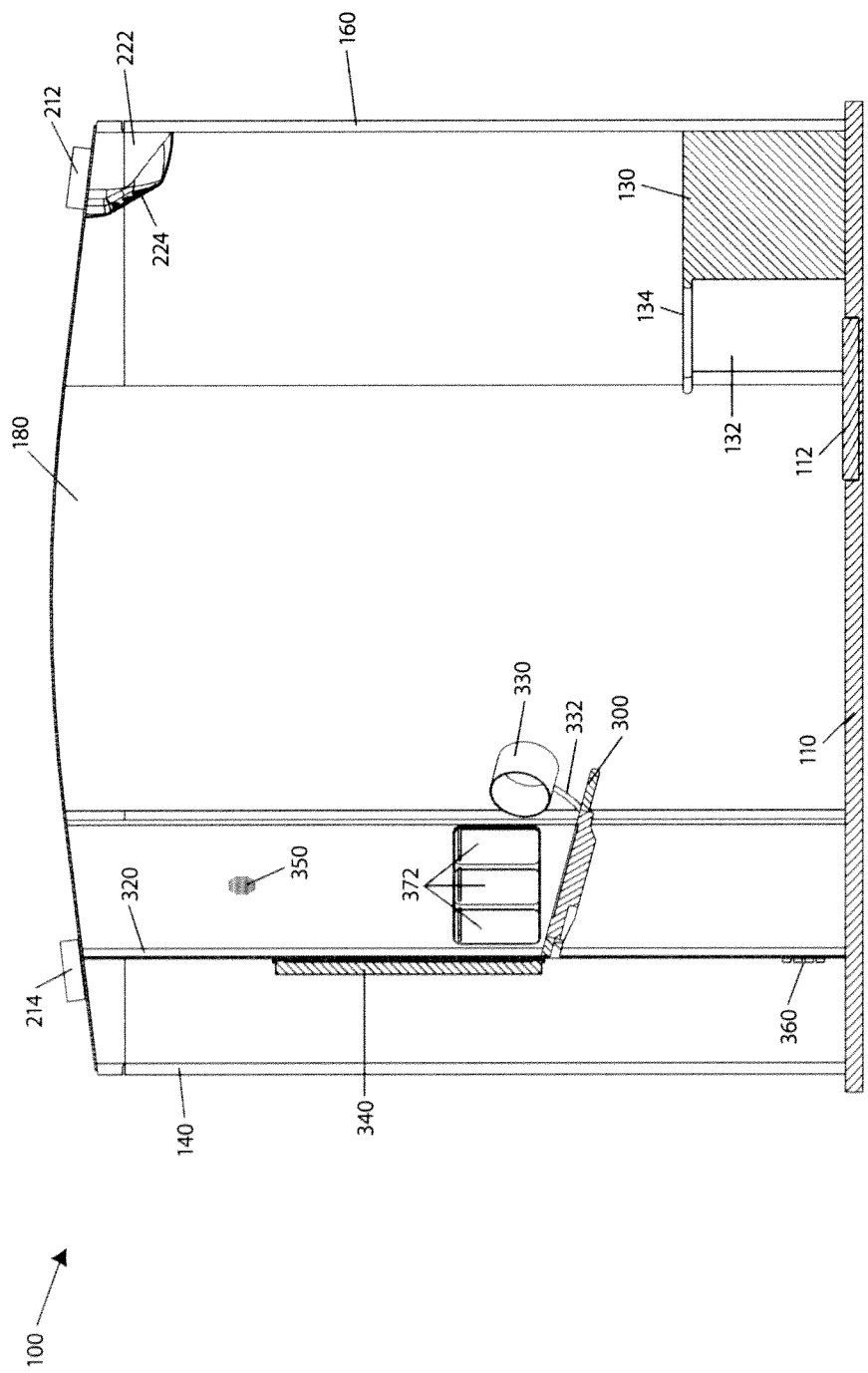
FIG. 9 is a cross-section view along line 9-9 of FIG. 8.
Figure 10:
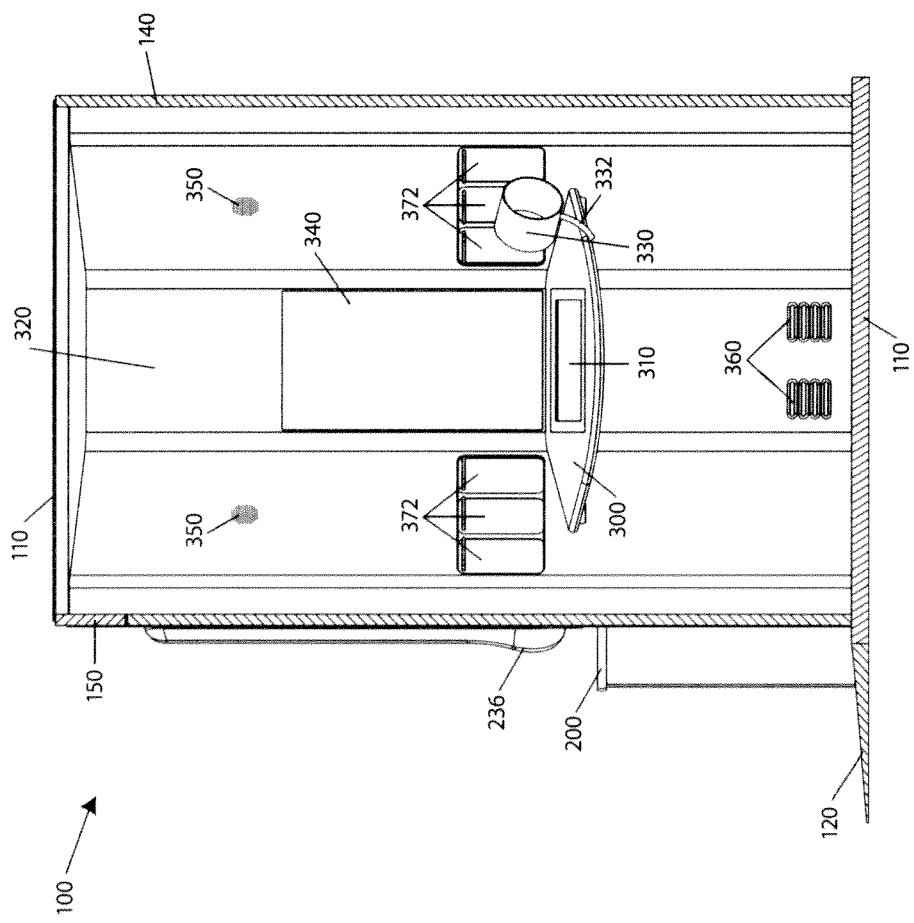
FIG. 10 is a cross-section view along line 10-10 of FIG. 8.
Figure 11:
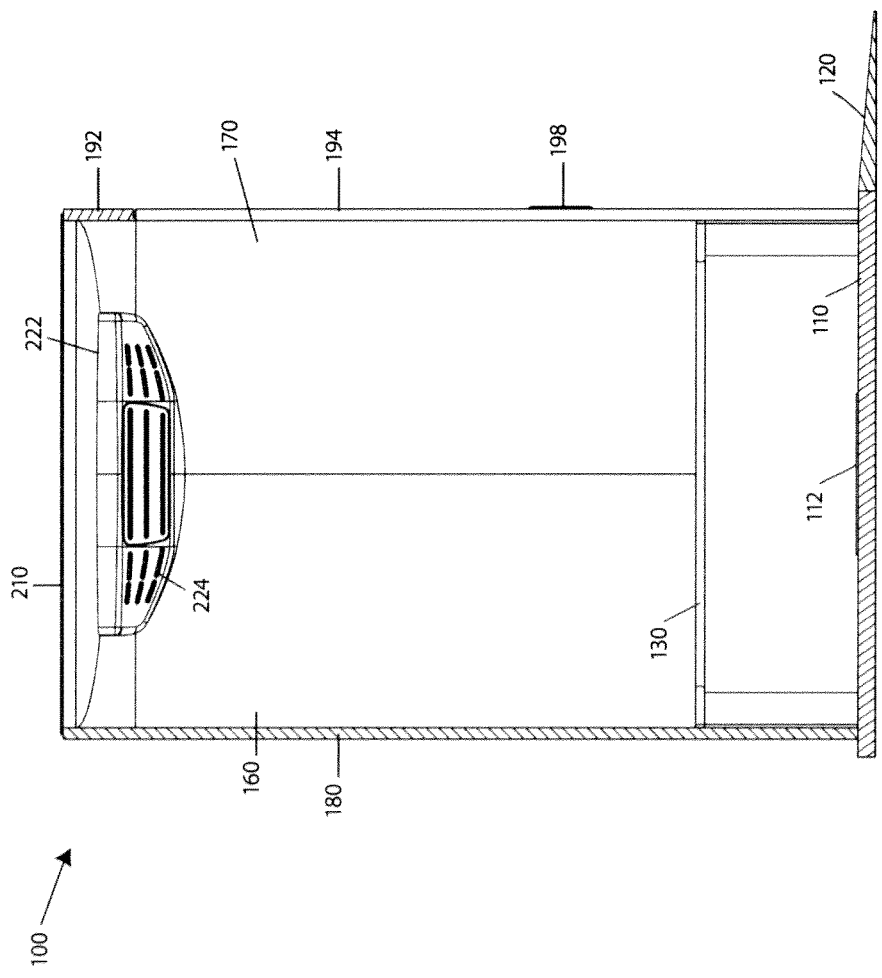
FIG. 11 is a cross-section view along line 10-10 of FIG. 8 viewed from the opposite direction; and, FIG. 12 is a front-side elevation view of the medical kiosk of FIG. 1.
Figure 12:
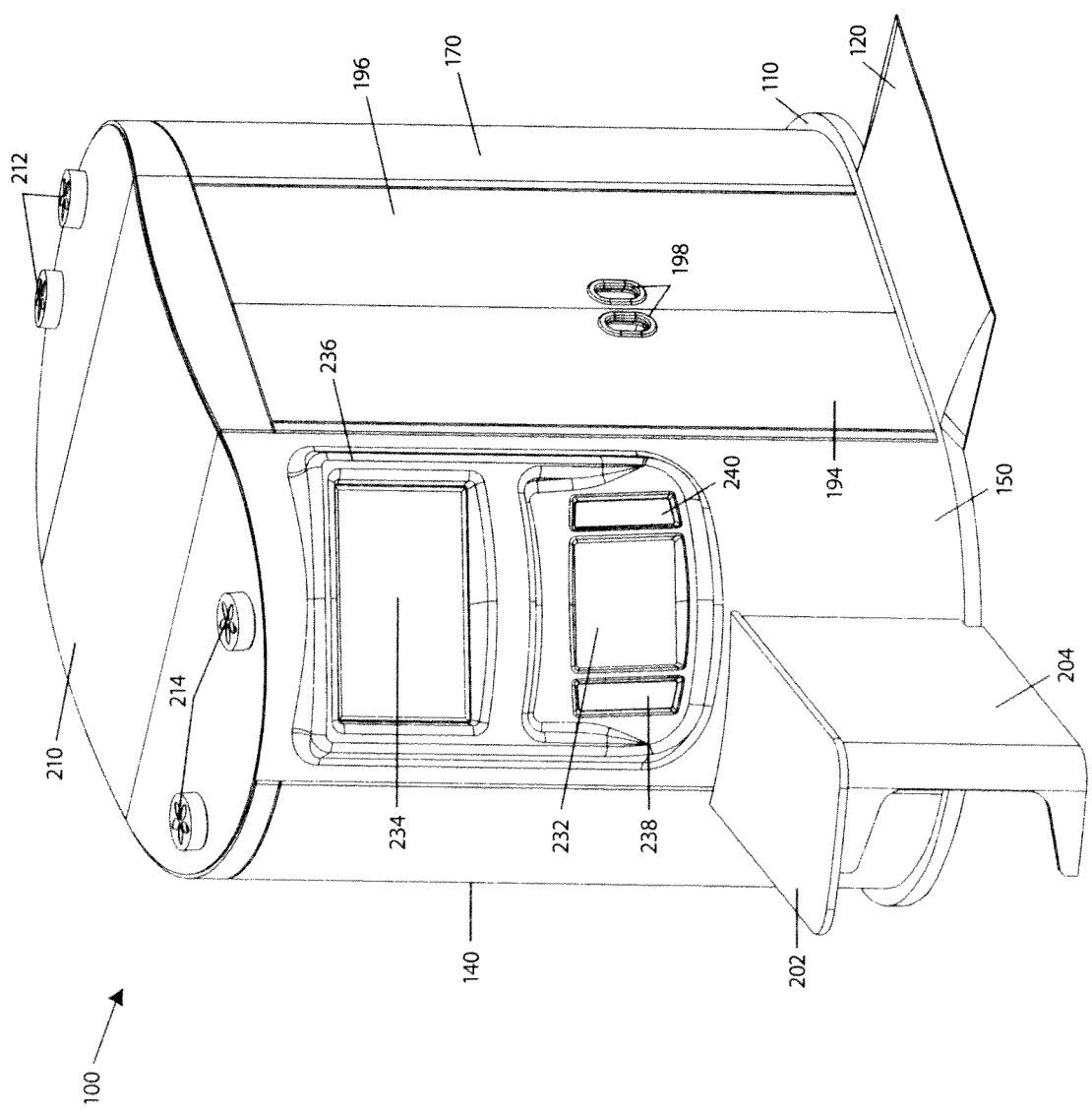

Referring now to FIGS. 9 and 10, a non-limiting interior front region of the medical kiosk is illustrated. A desk top 300 is used to support one or more touch pads 310 or keyboards positioned on the desk top. The shape, thickness and size of the desk top are non-limiting. The desk top is illustrated as secured to or formed on the front interior wall 320; however, this is not required. The desk top can have one or more support legs, not shown; however, this is not required. The one or more touch screens or keyboards on the desk top can be secured to the desk top; however, this is not required. The desk top is illustrated as sloping downward toward the front edge; however, this is not required. The size, shape and thickness of the one or more touch screens or keyboards are non-limiting. The one or more touch screens or keyboards are designed to be used by a user to enter various types of information (e.g., quality survey, patient history, patient medical information, payment information, questions to medical provider, etc.) before, during and/or after receiving medical services. The desk top can optionally include one or more other devices (lights, buttons, switches, camera, speakers, microphone, scanner, receiver, transmitter, credit card/debit card or other some other card reader, smart phone or other smart device reader/scanner, finger and/or eye scanner, shelf, printer, storage cavity, motion sensor, sound sensor, temperature sensor, logos, scanner, etc.); however, this is not required.

A chair, not shown, can be provided to enable the user to sit when using the medical kiosk. The chair can be a free standing chair or be connected to the medical kiosk.

A blood pressure cuff 330 can be connected to the desk top; however, this is not required. The blood pressure cuff is illustrated as support by a cuff arm 332. The cuff arm can optionally be mounted to the desk top to enable the blood pressure cuff to be moved from side to side of the desk top; however, this is not required. Such movement of the blood pressure cuff enables the blood pressure cuff to be positioned so that the left or right arm of a user can be inserted into the blood pressure cuff when the user is facing the desk top. As can be appreciated, when a blood pressure cuff is included in the medical kiosk, it can be mounted and/or positioned in the medical kiosk in a variety of ways. Information to and from the blood pressure cuff, when used, can be transmitted by wire or wirelessly to one or more computers, processors, storage devices, etc. in the medical kiosk and/or to a location remote from the medical kiosk.

One or more monitors or display screens 340 can be positioned on the front interior wall 320. As can be appreciated, one or more monitors or display screens can be positioned on other or additional locations in the medical kiosk. The shape, size and thickness of the one or more monitors are non-limiting. The monitor is generally used to view the one or more medical providers when the user is located in the medical kiosk. The one or more monitors can also or alternatively display other or additional information (e.g., instructions, questions, general medical information, time, output or results of examination of user, advertisements, information about the medical kiosk, information being displayed and/or entered by the user on the touchscreen, etc.).

One or more cameras (e.g., video camera, etc.) can be positioned on the front interior wall and/or be embedded in the one or more monitors or display screens 340. As can be appreciated, one or more cameras can be positioned on other or additional locations in the medical kiosk. The one or more cameras enable pictures of the user in the medical kiosk to be transmitted to a remotely located medical provider. The remotely located medical provider also typically includes a camera at his/her location so that pictures of the medical provider can be transmitted to the one or more monitors or display screens 340 in the medical kiosk. Such an arrangement can allow for real-time or near real-time video conferencing between the user and medical provider while the user is located in the medical kiosk. The one or more cameras can have other or additional functions (e.g., determine height of user when standing on scale or other locations in the medical kiosk, view one or more regions of user so as to provide a medical examination of the user in the medical kiosk, monitor occupancy of the medical kiosk, provide security monitoring for the medical kiosk, etc.). The one or more monitors or display screens 340 in the medical kiosk can also be used to replay one or more portions of the video conference between the user and medical provider after the secession with the medical provider has ended. Such a feature enables the user to review or again listen to instruction, advice, etc. provided by the medical provider to the user. This video playback feature can be limited to being viewed by the user while the user remains in the medical kiosk, or can also or alternatively be accessed be the user after the user exits the medical kiosk. If the user is able to access the recorded video conference outside the medical kiosk, the video file can 1) be accessed from some central server, 2) electronically sent to a person computer, mobile device, tablet, laptop, etc., and/or 3) mailed to the user (e.g., DVD, Blu-ray disk, video tape, USB jump drive, etc.).

One or more speakers 350 can be positioned on the front interior wall of the medical kiosk. As can be appreciated, one or more speakers can be positioned on other or additional locations in the medical kiosk. The speakers can be used to enable a user in the medical kiosk to listen to what the medical provider is saying to the user. One or more microphones are generally included in the medical kiosk to enable the user to verbally communicate with the medical provider. The medical kiosk can optionally include a braille keyboard and/or reader to enable the visually and/or hearing impaired to communicate with a medical provider while in the medical kiosk. The speakers can also or alternatively be used to play background music, sound an alarm, etc.

The front interior wall can optionally include one or more air vents 360. The one or more air vents, when used, can enable air to enter or exit the interior of the medical kiosk to thereby provide circulation in the medical kiosk. As illustrated in FIGS. 8-10, the air flow into the medical kiosk is provided by fan systems 212. Fan systems 212 draw air into the medical kiosk and cause the air to flow through vents 224 in shroud 222 of the UV sanitizing system. The air continues to flow in the interior of the medical kiosk and into air vents 360. The air travels upwardly an interior wall space of the medical kiosk to provide cooling to monitors 340 and 234 and to the electronic equipment that is positioned in or near the inner space, and then out from the medical kiosk via fan systems 214. As can be appreciated, other or additional air flow paths can be created in the medical kiosk. As can be appreciated, one or more air vents can be located in other or additional regions of the medical kiosk.

One or more equipment chambers 370 can be positioned on or near the front interior wall. The equipment chambers are used to store one or more medical devices (e.g., stethoscope, otoscope, thermometer, dermascope, spirometer, pulse oximeter, heating pad, magnifying glass, tongue depressor, tweezers, blood glucometer etc.). The one or more equipment chambers can also or alternatively be used to include other types of materials (e.g., tissue, Band-Aid, gauze, cotton ball, disinfecting wipe, cortisone cream, anti-biotic cream/ointment, cotton swab, fabric wrap, etc.). The one or more equipment chambers generally include a door 372 to limit access to the one or more equipment chambers; however, this is not required. The door, when used, can be manually openable/closeable, and/or the doors can be controllably opened/closed remotely by the medical provider and/or attendant. Generally, the doors are controllably opened and/or unlocked by the medical provider during the examination of the user in the medical kiosk. After the user has left the medical kiosk, the attendant can enter the medical kiosk, and then clean the medical equipment that was handled or used by the prior user and/or dispose of and/or replace items that were used and/or handled by the prior user. Thereafter, the attendant can restock, replace, and/or reposition the medical equipment and/or non-medical equipment in the equipment chambers and close the equipment chamber doors prior to the next user entering the medical kiosk. One or more types of medical equipment can be designed to transmit information by wire or wirelessly to electronic components in the medical kiosk and/or to the remotely located medical provider. As illustrated in FIG. 10, six equipment chambers having doors are included in the medical kiosk, three on each side of the desk top 300. As can be appreciated, a larger or smaller number of equipment chambers can be used. As also can be appreciated, some or all of the equipment chambers can be absent doors. The doors on the six equipment chambers are designed to be unlocked and/or opened remotely by the medical provider. The doors are designed to automatically lock closed when the doors are closed by the attendant after the user has left the medical kiosk; however, this is not required. Each of the six equipment chambers is designed to include a different piece of medical equipment, namely a stethoscope, an otoscope, a thermometer, a dermascope, a spirometer, and a pulse oximeter. As can be appreciated, a larger or smaller number of medical equipment can be used in the medical kiosk and/or different types of medical equipment can be included in the medical kiosk.

The medical kiosk and method for using the medical kiosk are a novel and advanced healthcare delivery system wherein patients and physicians can engage in real-time interactive consultations, providing convenient and affordable healthcare services. The medical kiosk includes the latest technologies in medical devices, video conferencing, and VOIP telephony so that the medical kiosk can extend traditional healthcare to convenient retail pharmacy locations or other locations in a user's neighborhood, therein enabling a user to see a medical provider and obtain a prescription, if required, in a fast and convenient manner.

Some advantageous aspect of the medical kiosk and medical method are:
  Patient Portal (Cloud Based).
  Doctor Portal (Cloud Based).
  Integrated Care Station.
  Facilitates Efficient Delivery of Basic Healthcare Delivery.
  Automates All Aspects of a Check Up.
  Easy Check-In.
  Vital Signs Capture.
  Prescription Generation.
  Post Care and Outcomes.
  Convenient Locations Where Consumers Want To Be.
  Video playback of the recorded session between the user and medical provider.

The medical kiosk and medical method can be used to provide primary and/or urgent care services in four (4) simple steps:
  Step 1—Patient requests appointment via web portal or walks to a medical kiosk and completes check in criteria.
  Step 2—Doctor receives eligible request and accepts.
  Step 3—Patient visits the medical kiosk and has a private appointment with a doctor via the doctor terminal.
  Step 4—Visit is completed. The medical kiosk and/or medical provider can then provide additional care/services that include: prescription, billing information, education, follow up and/or EMR/PHR entry. The medical provider can cause the medical kiosk to printout a prescription and/or directly send the prescription request to a pharmacy. The medical kiosk can print out a bill after the medical services are provided and/or accept payment prior to or after medical services are provided. The medical kiosk can be designed to accept and/or process medical insurance information provided by the user. The medical kiosk can print out and/or display education materials/information relevant to/requested by the user and/or provided by the medical provider. The medical kiosk and/or medical provider and/or attendant can schedule a follow-up visit for the user. Email, twitter, Facebook, phone and/or mail reminders can be sent to the user regarding scheduled and/or follow-up visits. The medical provider and/or attendant can schedule a visit with another medical provider and/or admit the user to the hospital, contact an ambulance, etc. during or after the visit to the medical kiosk.

Advantageous portal features of the medical kiosk and associated medical method are:
  Practice Management Engine.
    Appointments Scheduling Engine.
    Online Eligibility, Claims, and Billing Engine.
    ePrescribing with Alerts and Reminder Engine.
    Medical Records Interface and Access.
      Personal Health Record (PHR).
      Electronic Medical record (EMR).
      Rules-Based Care Plans.
      Rules-Based Education.
  Check In Pathway to Care Engine.
  Secure Video Conferencing Engine.
  Documentation Module.
    Appointment Storage and Analysis.
  Education and Post Care.

Some non-limiting advantages to patients by use of the medical kiosk and medical method are:
  Convenient.
    Closer to home.
    Saves time.
    Language and culture friendly.
  Better Access.
    Personal doctor available while traveling.
    Larger selection of doctors.
    Not limited by doctor's visitation schedule.
  More Accurate.
    Review record of appointment.
    Automatic data entry into PHR.
  Less Exposure to Illness.

Some non-limiting advantages to medical providers by use of the medical kiosk and medical method are:
  Higher Revenues.
    More appointments/day.
    Less traveling.
  More Accurate.
    Review record of appointment.
    Automatic data entry into EMR/HER.
  Integrated Care.
    Referral and transfer.
  Load Balancing.
    Appointment load can be shared with other doctors regardless of location.

Some non-limiting advantages to payers by use of the medical kiosk and medical method are:
  Change in Status.
    Transition from Payer to Provider.
  Market Leverage.
    New Business Model.
    Call Center based Nurse Practitioner.
  Efficiency.
    Market Demand.
    Less Overhead.
    Scalability.
    Less Liability.

The medical kiosk of the present invention is an Integrated Care Terminal that is a highly equipped doctor's office that is built and designed to deliver urgent and minor medical care in the field utilizing a centralized team of doctors for the evaluation and treatment of patients. The medical kiosk can be fitted with the latest FDA approved medical devices used by doctors today.

Employing the latest technology that is used in physician offices and emergency rooms, the medical kiosk is able to allow patients to obtain appropriate care in locations that are convenient, accessible, and more affordable.

The medical kiosk is designed to be a comfortable, self-contained, secure, sanitary, soundproof kiosk that is approximately 5 feet wide and 9½ feet long. The medical kiosk is made of extruded plastics and related components. The interior of the medical kiosk can contain one or more of the following integrated medical devices:

- Thermometer (e.g., temperature taken via ear, temperature taken via ear, IR thermometer to scan head or other area of body, etc.).
- Scale built into the patient seat or floor for measuring the patient's weight.
- Otoscope—for examining the middle ear, exterior ear, nasal passages, mouth and throat.
- Oximeter which measures the blood oxygen saturation.
- Stethoscope for evaluation of heart, lung and bowel sounds.
- Blood Pressure Cuff to measure blood pressure.
- EKG which provides a snapshot of the heart rhythm and data regarding stress or injury to the heart muscle.
- Spirometer and transducer for measuring lung function.
- Blood glucose measuring device or monitor.
- Retinal scan device (e.g., Itronix retinal scan device, etc.).

A nurse, nurse assistant, attendant, etc. who resides outside the medical kiosk can be responsible for answering user questions, assisting with user registration/payment, thoroughly clean the medical kiosk after each use, and restock and/or reset the medical kiosk after each use. The cleaning of the medical kiosk can include sanitizing the seat and all instruments as well as ensuring the medical kiosk is free of debris and any patient belongings. The medical kiosk can also be designed to be automatically sterilized after one or more users use the medical kiosk by utilizing a chemical mist sterilization technology and/or UV sterilization technology. The nurse, nurse assistant, attendant, etc. can also ensure that any insurance forms required by the user/patient for reimbursement are provided via a printer or some other means contained in the exterior and/or interior of the medical kiosk.

The medical kiosk can also contain a computer, which is connected to the internet and powers the one or more monitors and/or other type of equipment in the medical kiosk; however, this is not required. The exterior monitor on the medical kiosk can be used for patient registration and appointment selection that can be conducted in a touch screen format.

The method for providing medical services via a medical kiosk regarding protocols for scheduling, diagnosing, delivering and documenting telemedicine primary care can include:

a. Medical Provider web portal—this application is used by the medical provider to provide clinical services. The application contains all that the medical provider requires to diagnose, deliver care and document the clinical episode. It runs on the physician's computer and can be integrated with the leading EMR applications via HL/7, etc. One part of the medical provider portal is the telemedicine protocols and interview wizards which take the medical provider through a guided process for the clinical tele-services. [Robert—Steve Barrett questioned whether this section and following sections were correct]

b. Patient web portal—this application is used by the patient to register with a medical kiosk and also captures the patient's medical history. It includes all the information required to administer clinical services to the patient. This includes financial/billing information and a Healthspot Electronic Medical Record (EMR), which can be accessed by the patient and the medical providers.

c. Integrated videoconferencing software—this application supports the live patient-clinician interaction required for delivery of the clinical services. It uses a secure connection to the servers and the provider via an internet connection.

To use a medical kiosk, the users/patients may go through one or more of the following steps:

a. Go Online, register and schedule an appointment at the nearest terminal or walk-in and register at the medical kiosk.

b. Use our online scheduling engine to select an appointment time.

c. Input insurance, preferred pharmacy location and billing information, and remit payment.

d. Complete pre-appointment pathway to care.

e. Visit a medical kiosk and see a medical provider via the integrated care terminal.

f. Pick up prescription, if indicated, at the pharmacy of choice.

g. Use website to manage user's care until user is better.

The following example is a non-limiting example as to what one user may encounter when using the medical kiosk of the present invention:

Jane Doe is not feeling well, suffering from severe nasal congestion and "cold symptoms" for several days. She realizes she should seek care, but finds it frustrating to schedule an appointment with her primary care physician and knows that this is not an appropriate reason to visit her local ER. However, she recently became aware of a medical kiosk in her neighborhood grocery store, and decides to drive to the store a few minutes from her home to see if she can get a walk-in appointment. Upon arrival, Jane is met by the attendant who helps her register at the exterior of the medical kiosk for the next available appointment in a few minutes. She completes the basic information about her complaint in a short guided questionnaire via the monitor on the exterior of the terminal. The intake questionnaire captures demographic information include some or all of the following information: fingerprint, simple medical history/medications, current symptoms, preferred pharmacy, insurance information, and a fixed fee credit card payment for the visit. Information is gathered and stored securely to facilitate future visits. Jane then has a seat at a small waiting area near the medical kiosk. When the previous appointment ends by another user, Jane witnesses the attendant cleaning the appropriate surface areas of the interior of the medical kiosk, changing the protective covers of the instruments that were used, and hears a sterilizing mist sprayed into the medical kiosk.

Jane then swipes her fingerprint to verify her identity, enters the medical kiosk and is seated. Once her identity is verified, she is weighed by the scale and receives a friendly greeting from the live medical provider on the television monitor. The medical provider has already spent some time scanning Jane's medical history, current medications and symptoms. The medical provider then interviews Jane following the diagnostic telemedicine protocols, which are queued up, on the medical provider's home or office computer. Jane can see and speak to the medical provider and the medical provider can see and speak to Jane via the monitor facing Jane's chair.

After the medical provider has spoken to Jane and taken a medical history, he suspects a possible sinus infection. The medical provider then clicks on a button in the physician computer application, which creates a signal (e.g., green light, etc.) to open a door to a medical device cavity or compartment on the medical kiosk or turns on a light in the medical kiosk to identify the compartment that includes the otoscope. The medical provider than instructs Jane to gently insert the device in her nose and takes a picture of her nasal mucosa. The picture is then displayed on the side of the monitor where Jane can see it. The medical provider proceeds to instruct Jane to use the instrument to look in her ears and throat. The pictures are all queued on the side of the monitor. The medical provider then uses a tele-pen to highlight areas on the pictures of Jane's throat and nasal passages, which are inflamed and indicative of an upper respiratory infection. Based on her symptoms and the examination, the medical provider tells Jane he believes that she has a sinus infection.

Jane sees the pictures and feels comfortable with the diagnosis of a sinus infection, as she was able to witness firsthand the pictures with the telestrator. The medical provider thanks Jane for her visit and follows the protocols for wrapping up the visit. A prescription for the appropriate antibiotic is e-prescribed by the medical provider and sent electronically to the pharmacy of Jane's choice, which in this case happens to be the pharmacy within the grocery store. Upon exiting the terminal, Jane receives a completed Hgfa insurance form from the attendant, which she can use to file with her insurance company for reimbursement. Jane then walks over to the pharmacy and waits on her prescription, which is available ten minutes later. She returns home and begins taking the medication to cure her sinus infection.

Some of the non-limiting features of the medical kiosk are:
Integrated Medical Devices.
Exterior Check-In Station.
Patient Waiting Area.
Integrated Wi-Fi Hot Spot.
Touch Screen User Interface.
HIPAA Compliant Design.
Instant Sterilization.
Video/Audio Conferencing.
Flexible Access.
   Handicap.
   Parent and Child.
Modular design for Pharmacy door deployment.
Small Footprint.
Fully Integrated Interior Design.
Expandable Device Rail.
Secure PC storage with access.
Open design feels comfortable.
Payment and Signature.
Finger Print Reader.
Integrated Printer.
Integrated Medical Devices.
   Thermometer—(e.g., temperature taken via ear, temperature taken via ear, IR thermometer to scan head or other area of body, etc.
   Scale built into the patient seat or floor for measuring the patient's weight.
   Otoscope—for examining the middle ear, exterior ear, nasal passages, mouth and throat.
   Oximeter which measures the blood oxygen saturation.
   Stethoscope for evaluation of heart, lung and bowel sounds.
   Blood Pressure Cuff to measure blood pressure.
   EKG which provides a snapshot of the heart rhythm and data regarding stress or injury to the heart muscle.
   Spirometer and transducer for measuring lung function.
   Blood Glucose measurement device and/or monitor to measure blood glucose levels.
   Retinal scan device to view structures in the eye.
Exterior Check-In Station—A monitor and keyboard is generally mounted on the outside of the medical kiosk to allow for new user/patient registration and check in. The station can be designed to take payment and/or a fingerprint. The station generally is located away from the entrance to the medical kiosk to allow a degree of separation from the patient inside the medical kiosk. The attendant can use this station for her work.
Patient Waiting Area—Can include a small area to put a few chairs outside the medical kiosk to act as a waiting area.
Integrated Wi-Fi Hot Spot—In order to minimize network connection cost, a Wi-Fi hot spot can partner with an ISP of choice (AT&T, Verizon, Sprint, T-Mobile, etc.).
Touch Screen User Interface—The patient can be allowed to interact while inside the medical kiosk by use of a touch screen interface.
HIPAA Compliant Design—HIPAA requires patient information to be secure. This will mean the medical kiosk will generally be sound proof and a passerby cannot see in and see any patient information. The medical kiosk generally is fully enclosed and lockable, but can allow exterior access in case of emergency.
Instant Sterilization—Because of the many germs and other contaminants that will be inside the medical kiosk, a sterilization technology can be used in the medical kiosk. One type of sterilization system that can be used is a built-in sanitizing misting system that dispenses from a series of misters between every appointment. Another or additional sterilization system that can be used is a UV lighting system that can be blasted between appointments. Other techniques and technologies can also or alternatively be used. The attendant can have the ability to activate one or more sterilization systems (e.g., via button, computer, etc.). The attendant can be required to keep track of records about the sanitization process and can ensure that the doors to the medical kiosk are closed/locked during the sterilization process.
Video/Audio Conferencing—The patient will communicate with the medical provider via video and audio conferencing technology. This environment can make the patient feel as close to the medical provider as actually being present as possible. A two-way glass can be used to place the camera in the center of the monitor to keep the patient looking head on, versus the Skype and current video conferencing solutions that keep users looking at the camera and back to the monitor.
Flexible Access—The medical kiosk should have a large enough door to accommodate a wheel chair. It should also be large enough inside to allow a parent to sit with a child and not feel constrained.
Modular design for Pharmacy door deployment—Most Pharmacies today only have a standard door. The medical kiosk is built in a manner that allows it to enter through the door and quickly be assembled.
Small Footprint—Because of the cost of retail space, the medical kiosk will be small enough to fit in most locations (e.g., 4-6 ft. wide and 7-10 ft. length).
Fully Integrated Interior Design—The interior of the medical kiosk can be designed to be cleaner, sleeker, nicer, more luxurious, than the experience they get at the average doctor's office.
Expandable Device Rail—The medical kiosk can include the latest medical devices and update such medical devices in a more rapid manner than the average doctors' office. The medical kiosk can include a mounting rail type system that allows medical devices in the medical kiosk to be easily accessed by the user. An indicator, such as a light, can be used to notify which medical device is to be used by the user.
Secure PC storage with access—Because uptime of the software is so important, electronics can be inserted in a compartment in the medical kiosk. Such area generally should be secure, cooled, and easily accessible for service.

Open design feels spacious—The medical kiosk is generally designed to feel bigger than it is such as by providing a glass window that wraps around the back half of the kiosk.

Payment and Signature—The medical kiosk can include an integrated credit card swipe for payment, and a signature pad for medical authorization.

Finger Print Reader—A finger print reader can be included on the medical kiosk to confirm patient ID under HIPAA.

Integrated Printer—An integrated printer can be included in the medical kiosk to print medical and insurance forms and/or receipts and/or prescription. The printer can also print coupons based upon diagnosis to promote product sales. Our software can be included to inform the attendant of low paper in the paper.

Video Playback—The recorded medical session can be partially or fully reviewed by the user to enable the user to in listen to information, instructions and/or advise from the medical provider. As can be appreciated, the video playback feature can also or alternatively be used for auditing purposes, compliance purposes, security purposes, quality control purposes, etc.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween. The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

We claim:

1. A medical kiosk having a modular configuration and designed to provide tele-med services to a user, said medical kiosk including first and second front panels, first and second rear panels, an interior chamber, a chamber access opening, a side wall and a door system, and a user video conferencing system in said interior chamber, said user video conferencing system designed to enable the user in said interior chamber to have a real-time or near real-time teleconference with a medical provider located remotely from said medical kiosk, said front and rear panels at least partially forming a wall of said interior chamber, said first and second front panels having the same foot print, said first and second rear panels having the same foot print, said first and second front panels are designed to be interchangeable with one another when assembling said medical kiosk, said first and second rear panels are designed to be interchangeable with one another when assembling said medical kiosk, said side wall and door system having the same foot print and are interchangeable with one another when assembling said medical kiosk, said user video conferencing system includes a display monitor designed to enable the user in said interior chamber to view the remotely located medical provider, a camera designed to enable the remotely located medical provider to view the user in said interior chamber, a microphone designed to enable the user in said interior chamber to communicate with the remotely located medical provider, and a user input device, said interior chamber includes a plurality of medical devices, at least one of said medical devices is designed for use by the user in said interior chamber to provide information to the medical provider about the user to enable the medical provider to provide real-time or near real-time medical advice to the user in the interior chamber, at least one of said medical devices located in said interior chamber is selected from the group consisting of a stethoscope, a thermometer, a spirometer, and a pulse oximeter, said interior chamber including a cleaning or sanitizing system to treat the complete interior chamber to kill, neutralize, or combinations thereof at least some germs, micro-organisms, or combinations thereof in said interior chamber, said cleaning or sanitizing system including a system selected from the group consisting of a UV system and a mist system, said interior chamber includes six remotely controlled medical compartments, each of said remotely controlled medical compartments includes at least one of said medical devices, each remotely controlled medical compartment including one of said medical devices that is different from any other of said medical devices located in any other of said remotely controlled medical compartments, each of said remotely controlled medical compartments includes a movable and lockable door that limits access to said at least one medical device in said medical compartment, said door moveable between a closed position and an open position, said closed position of said door limiting access to said medical device in said remotely controlled medical compartment, said open position allowing access to said medical device in said remotely controlled medical compartment, each of said doors on each of said remotely controlled medical compartment is selectively unlockable by said medical provider to cause said door to move from said closed position to said open position.

2. The medical kiosk as defined in claim 1, wherein each of said first and second front and rear panels extending between a base and a top of said medical kiosk.

3. The medical kiosk as defined in claim 1, wherein each of said remotely controlled medical compartments includes a different one of said medical devices selected from the group consisting of a stethoscope, an otoscope, a thermometer, a dermascope, a spirometer, and a pulse oximeter.

4. The medical kiosk as defined in claim 1, wherein said door system including said chamber access opening.

5. The medical kiosk as defined in claim 1, includes a registration station positioned outside of said interior chamber and positioned on at least one of said front panels, said registration station including a user input system and a registration video display that enables the user to enter information about the user prior to having said real-time or near real-time tele-conference with a medical provider.

6. The medical kiosk as defined in claim 1, including a floor panel, said medical kiosk including one or more accessories positioned at least partially on or in said floor panel, said accessories selected from the group consisting of a bench and a scale.

7. The medical kiosk as defined in claim 1, including a ceiling panel and a fan system located on said ceiling panel, said fan system designed to draw air into said interior chamber, draw air out of said interior chamber or combinations thereof, said fan system including a filtering system.

8. The medical kiosk as defined in claim 1, including an attendant's desk positioned outside said interior chamber.

9. A medical kiosk designed to provide tele-med services to a user, said medical kiosk including an interior chamber, a chamber access opening, first and second front panels first and second rear panels, a side wall and a door system, and a user video conferencing system in said interior chamber, said first and second front panels are designed to be interchangeable with one another when assembling said medical kiosk, said first and second rear panels are designed to be interchangeable with one another when assembling said medical kiosk, said side wall and door system having the same foot print and are interchangeable with one another when assembling said medical kiosk, said user video conferencing system designed to enable the user in said interior chamber to have a real-time or near real-time tele-conference with a medical provider located remotely from said medical kiosk, said user video conferencing system includes a display monitor designed to enable the user in said interior chamber to view the remotely located medical provider, a camera designed to enable the remotely located medical provider to view the user in said interior chamber, a microphone designed to enable the user in said interior chamber to communicate with the remotely located medical provider, and a user input device, said interior chamber includes a plurality of medical devices, at least one of said medical devices is designed for use by the user in said interior chamber to provide information to the medical provider about the user to enable the medical provider to provide real-time or near real-time medical advice to the user in the interior chamber, said interior chamber includes, said interior chamber includes six remotely controlled medical compartments, each of said remotely controlled medical compartments includes at least one of said medical devices, each remotely controlled medical compartment including one of said medical devices that is different from any other of said medical devices located in any other of said remotely controlled medical compartments, each of said remotely controlled medical compartments includes a movable and lockable door that limits access to said at least one medical device in said medical compartment, said door moveable between a closed position and an open position, said closed position of said door limiting access to said medical device in said remotely controlled medical compartment, said open position allowing access to said medical device in said remotely controlled medical compartment, each of said doors on each of said remotely controlled medical compartment is selectively unlockable by said medical provider to cause said door to move from said closed position to said open position, said interior chamber including a cleaning or sanitizing system that includes a UV system.

10. The medical kiosk as defined in claim 9, wherein at least one of said plurality of said medical devices located in one of said remotely controlled medical compartments is selected from the group consisting of a stethoscope, an otoscope, a thermometer, a dermascope, a spirometer, and a pulse oximeter.

11. The medical kiosk as defined in claim 10, including a registration station connected to an outside surface of said interior chamber, said registration station including a second user input system and a registration video display that enables the user to enter information about the user and to enable the user to enter payment information for services to be provided by the medical provider prior to entering said interior chamber and having said real-time or near real-time tele-conference with the medical provider.

12. The medical kiosk as defined in claim 11, wherein said interior chamber includes a lockable door that provides access to said interior chamber and limits access to said interior chamber when said lockable door in a closed position.

13. The medical kiosk as defined in claim 12, wherein said cleaning or sanitizing system located at or near a ceiling of said kiosk.

14. The medical kiosk as defined in claim 13, wherein said front and rear panels at least partially forming an interior wall of said interior chamber, each of said first and second front and rear panels extending between a base and a top of said medical kiosk, said display monitor and said camera positioned closer to said front panels than to said rear panels, said sanitizing system positioned closer to said rear panels than to said front panels, said lockable medical compartments positioned closer to said front panels than to said rear panels, at least one of said remotely controlled medical compartments positioned on one side of said display monitor and at least one of said remotely controlled medical compartments positioned on an opposite side of said display monitor.

15. The medical kiosk as defined in claim 9, including a registration station connected to an outside surface of said interior chamber, said registration station including a second user input system that enables the user to enter information about the user and to enable the user to enter payment information for services to be provided by the medical provider prior to entering said interior chamber and having said real-time or near real-time tele-conference with the medical provider.

16. The medical kiosk as defined in claim 9, wherein said interior chamber includes a lockable door that provides access to said interior chamber and limits access to said interior chamber when said lockable door in a closed position.

17. The medical kiosk as defined in claim 9, wherein said cleaning or sanitizing system located at or near a ceiling of said kiosk.

18. The medical kiosk as defined in claim 9, wherein said front and rear panels at least partially forming an interior wall of said interior chamber, each of said first and second front and rear panels extending between a base and a top of said medical kiosk, said display monitor and said camera positioned closer to said front panels than to said rear panels, said sanitizing system positioned closer to said rear panels than to said front panels, said lockable medical compartments positioned closer to said front panels than to said rear panels, at least one of said remotely controlled medical compartments positioned on one side of said display monitor and at least one of said remotely controlled medical compartments positioned on an opposite side of said display monitor.

\* \* \* \* \*